(12) United States Patent  (10) Patent No.: US 8,642,614 B2
Yin et al.  (45) Date of Patent: Feb. 4, 2014

(54) TOLL-LIKE RECEPTOR MODULATORS AND USES THEREOF

(75) Inventors: Hang Yin, Boulder, CO (US); Linda R. Watkins, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 17 days.

(21) Appl. No.: 13/498,070

(22) PCT Filed: Sep. 23, 2010

(86) PCT No.: PCT/US2010/050050
§ 371 (c)(1),
(2), (4) Date: Mar. 23, 2012

(87) PCT Pub. No.: WO2011/038152
PCT Pub. Date: Mar. 31, 2011

(65) Prior Publication Data
US 2012/0178774 A1  Jul. 12, 2012

Related U.S. Application Data

(60) Provisional application No. 61/244,997, filed on Sep. 23, 2009.

(51) Int. Cl.
*A61K 31/439* (2006.01)
*A61K 31/415* (2006.01)
*C07D 231/02* (2006.01)

(52) U.S. Cl.
USPC .......................... 514/282; 514/406; 548/375.1

(58) Field of Classification Search
None
See application file for complete search history.

(56) References Cited

U.S. PATENT DOCUMENTS

| | | | | |
|---|---|---|---|---|
| 4,457,933 | A * | 7/1984 | Gordon et al. | 514/282 |
| 6,977,300 | B2 * | 12/2005 | Kalla et al. | 544/269 |
| 2005/0113345 | A1 * | 5/2005 | Chow et al. | 514/114 |
| 2006/0173065 | A1 * | 8/2006 | Bezwada | 514/419 |

OTHER PUBLICATIONS

Youn et al.: "Cinnamaldehyde suppresses toll-like receptor 4 activation mediated through the inhibition of receptor oligomerization", Biochemical Pharmacology, Pergamon, Oxford, GB, 2007, vol. 75, No. 2, pp. 494-502.

Ii M. et al. "A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling", Molecular Pharmacology, 2006, vol. 69, No. 4, pp. 1288-1295.

* cited by examiner

*Primary Examiner* — Jason M Nolan
*Assistant Examiner* — Ana Z Muresan
(74) *Attorney, Agent, or Firm* — Don D. Cha; Hamilton DeSanctis & Cha, LLP

(57) ABSTRACT

The present invention provides a compound of the formula:

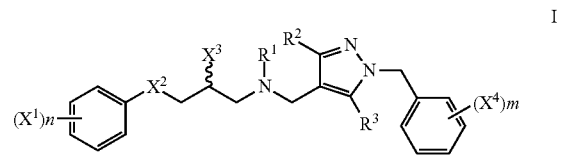

where n, m, $X^1$, $X^2$, $X^3$, $X^4$, $R^1$, $R^2$ and $R^3$ are those defined herein. Some aspects of the invention also provides methods for using these compounds and compositions comprising the same.

13 Claims, 4 Drawing Sheets

TOLL-LIKE RECEPTOR MODULATORS AND USES THEREOF

CROSS-REFERENCE TO RELATED APPLICATIONS

This application claims the priority benefit of U.S. Provisional Application No. 61/244,997, filed Sep. 23, 2009, which is incorporated herein by reference in its entirety.

STATEMENT REGARDING FEDERALLY FUNDED RESEARCH

This invention was made with government support under grant number RR025780 awarded by the National Institutes of Health. The government has certain rights in the invention.

FIELD OF THE INVENTION

The present invention relates to toll-like receptor modulators, compositions comprising the same, and methods for making and using the same.

BACKGROUND OF THE INVENTION

The pharmacology and treatment of pain has a very long and tumultuous history. Since the infancy of the use of opium poppy extracts to treat pain around 3500 BC, the search for treatments that provide effective relief from acute and chronic pain has continued to grow at an extraordinary rate. Today, pain still remains a significant public health issue with two-thirds of patients achieving little to no pain relief from the myriad of currently available pharmacotherapy and dosing regimens. The use of opioid (i.e., opiate) pharmacotherapy produces several rewarding and reinforcing side effects, which result in the drugs' diversion to abuse settings. Unfortunately, a significant side effect in attempting to improve patients' quality of life is that some become dependent to the treatments that were prescribed to help them. In recent years the misuse of opioids has risen drastically, leaving doctors and patients hesitant to treat pain to the fullest extent.

Therefore, there is a continuing need for compounds, compositions, and methods for treating pain that does not result in unwarranted dependency.

SUMMARY OF THE INVENTION

Some aspects of the invention provide various compounds, compositions comprising the same, and methods for using these compounds and compositions to modulate toll-like receptors (TLRs) as well as treating various clinical conditions associated with TLRs.

Other aspects of the invention provide a compound selected from the group consisting of:

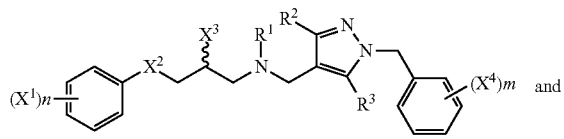

I and

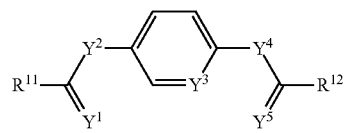

II where
each of n and m is independently an integer from 0 to 5;
each $X^1$ is independently alkoxide, optionally-substituted alkyl, or alkenyl;
$X^2$ is O, $NR^a$, or S;
$X^3$ is —$OR^b$, —$SR^b$, or —$NR^bR^c$;
each $X^4$ is independently halide or alkoxide;
each of $R^1$, $R^2$ and $R^3$ is independently hydrogen, or alkyl;
each of $Y^1$ and $Y^5$ is independently O or S;
each of $Y^2$ and $Y^4$ is independently O, S, or $NR^C$;
$Y^3$ is CH or N;
each of $R^a$, $R^b$, $R^c$, $R^1$, $R^2$, and $R^3$ is independently hydrogen or alkyl;
$R^{11}$ is cycloalkyl or alkyl;
$R^{12}$ is alkyl, optionally-substituted aryl, or cycloalkyl.

In some embodiments, the compound is of the formula:

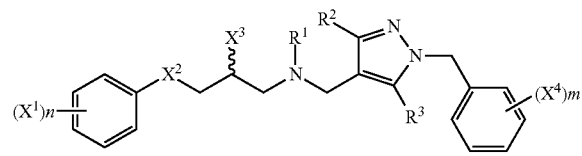

where
each of m and n is independently an integer of 0-5; typically each of m and n is independently an integer of 0-4; often each of m and n is independently an integer of 0-2; and
$X^1$, $X^2$, $X^3$, $X^4$, $R^1$, $R^2$, and $R^3$ are those defined in herein. Within these embodiments, in some instances $X^2$ is O. Still in other instances, $X^3$ is —OH. Yet in other instances, $R^1$, $R^2$ and $R^3$ are alkyl. Typically, $R^1$, $R^2$, and $R^3$ are methyl. Yet in other instances, $X^1$ is alkoxide, hetero-substituted alkyl or alkenyl-alkyl. Often $X^1$ is methoxide, methoxyethyl, or allyl. Still in other instances, $X^4$ is alkoxide, Cl, or F. Typically, $X^4$ is methoxide or Cl.

In other embodiments, the compound is of the formula:

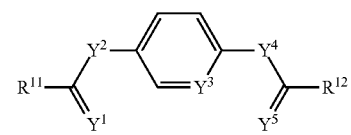

where
$Y^1$ and $Y^5$ are O; and
$R^{11}$, $R^{12}$, $Y^2$, $Y^3$ and $Y^4$ are those defined herein.
Within these embodiments, in some instances $Y^2$ is $NR^c$. Typically, $R^c$ is hydrogen. Yet in other instances, $Y^4$ is O or NH. Still in other instances, $R^{11}$ is adamantyl, n-butyl, iso-butyl, n-pentyl, or 1-ethylpropyl. In other instances, $R^{12}$ is alkyl, adamantyl, cyclohexyl, or optionally substituted phenyl. Often $R^{12}$ is iso-butyl, n-butyl, sec-butyl, tert-butyl, n-pentyl, cyclohexyl, adamantyl, phenyl, methoxyphenyl, or chlorophenyl.

Other aspects of the invention provide a method for modulating Toll-like receptor (TLR) comprising contacting a cell expressing a TLR with an effective amount of a compound disclosed herein. Typically, the compound is a TLR antagonist.

Still other aspects of the invention provide a method for treating a subject for a clinical condition associated with Toll-like receptor (TLR) activation. The method typically comprises administering to the subject a compound disclosed herein. Typically, the clinical condition comprises a condition associated with Toll-like receptor (TLR) mediated activation of glial cell. The clinical condition often comprises neuropathic pain, acute opioid analgesia, or a unwanted opioid side-effect, or a combination thereof. In other embodiments, the clinical condition comprises chronic pain, nociception, acute opioid analgesia, or a unwanted opioid side-effect, gastrointestinal pathologies, cardiovascular disease, diabetes, immune related conditions, systemic pathologies, neurodegeneration, induction of labor, fever, seizures, epilepsy, epileptogenesis, or a combination thereof. Often the unwanted opioid side-effect comprises opioid dependence, opioid reward, opioid induced respiratory depression, opioid induced ataxia, opioid induced hyperalgesia, opioid induced allodynia or hyperalgesia, opioid induced gastrointestinal disorders, narcotic bowel syndrome, opioid dysphoria, or a combination thereof.

Yet other aspects of the invention provide a method for treating a clinical condition associated with a TLR4/MD-2 interaction in a subject, said method comprising administering to the subject in need of such a treatment a TLR4/MD-2 interaction inhibitor. Often the clinical condition comprises neuropathic pain, acute opioid analgesia, or a unwanted opioid side-effect, or a combination thereof. In other embodiments, the clinical condition comprises chronic pain, nociception, acute opioid analgesia, or a unwanted opioid side-effect, gastrointestinal pathologies, cardiovascular disease, diabetes, immune related conditions, systemic pathologies, neurodegeneration, induction of labor, fever, seizures, epilepsy, epileptogenesis, or a combination thereof. Typically, the unwanted opioid side-effect comprises opioid dependence, opioid reward, opioid induced respiratory depression, opioid induced ataxia, opioid induced hyperalgesia, opioid induced allodynia or hyperalgesia, opioid induced gastrointestinal disorders, narcotic bowel syndrome, opioid dysphoria, or a combination thereof.

Still other aspects of the invention provide a composition comprising an opiate and a compound of the invention. In some embodiments, the opiate and the compound of the invention are intimately mixed. In other embodiments, the opiate and the compound of the invention are in separate forms. Generally, any opiate known to one skilled in the art can be used in the compositions (and methods) of the invention. Exemplary opiates include both (+)- and (−)-isomers. Typically, compositions (and methods) of the invention comprise an enantiomerically enriched, e.g., 90% ee or more, typically 95% ee or more, and often 98% ee or more (−)-opiate. Specific examples of suitable opiates include, but are not limited to, morphine, methadone, oxycodone, buprenorphine, fentanyl and pethadine/meperidine, amongst others.

Since the compounds of the invention potentiate the effect of the opiate typically the amount of opiate in the composition is less than the amount of opiate typically used in the absence of the compound of the invention. In some embodiments, the amount of opiate present in the composition is about 50% to about 100%, typically from about 75% to about 100%, and often from about 90% to about 100% relative to the recommended dosage of the opiate in the absence of the compound of the invention. Alternatively, the mole ratio of the opiate to the compound of the invention in the composition ranges from about 1000:1 to about 10:1, typically from about 100:1 to about 10:1, and often from about 50:1 to about 10:1.

Still other aspects of the invention provide methods for treating pain in a subject in need of such a treatment. Such methods typically include administering to the subject a combination of therapeutically effective amounts of an opiate and a compound of the invention. In some embodiments, the opiate and the compound of the invention are administered simultaneously or successively.

Yet other aspects of the invention provide methods for potentiating analgesic effects of an opiate compound. Such methods include co-administering to the subject an opiate and a therapeutically effective amount of a compound of the invention. The term "co-administered" refers the administering the opiate and the compound of the invention within a few hours of each other, e.g., within one or two hours, typically within an hour or less, often with a half an hour or less and more often within ten minutes or less. It should be appreciated that when the opiate and the compound of the invention are administered separately, the compound of the invention can be administered prior to or after administration of the opiate. In some embodiments, the opiate and the compound of the invention are administered substantially simultaneously. The terms "substantially simultaneously" and "simultaneously" refer to administering the opiate and the compound of the invention within five minutes, typically within three minutes, and often within one minute of each other. In some particular embodiments, the compound of the invention is administered prior to administering the opiate. In such embodiments, generally the compound of the invention is administered no more than 2 hours, typically no more than 1 hour, and often no more than 0.5 hour, prior to administering the opiate. Yet in other particular embodiments, the compound of the invention is administered after administering the opiate. In such embodiments, generally the compound of the invention is administered about 2 hours or less, typically 1 hour or less, and often 0.5 hour or less after administering the opiate.

Other aspects of the invention provide methods for reducing the side-effects of an opiate pharmacotherapy in a subject. Such methods typically include administering a therapeutically effective amount of a compound of the invention to the subject who is undergoing an opiate pharmacotherapy. In some embodiments, the methods also include administering from about 50% to about 100% of the opiate to the subject relative to the recommended dosage of the opiate in the absence of the compound of the invention. In some particular embodiments, the compound of the invention and the opiate are administered to the subject substantially simultaneously. Yet in other embodiments, the compound of the invention is administered no more than 2 hours, typically no more than 1 hour, and often no more than 0.5 hour prior to administering the opiate. Still in other embodiments, the compound of the invention is administered about 2 hours or less, typically about 1 hour or less, and often about 0.5 hour or less after administering the opiate.

(c) Compound A-1 to TLR4' LRR repeats, binding to the same cleft on the TLR4 surface to which MD-2 protein recognizes.

Figure 2:
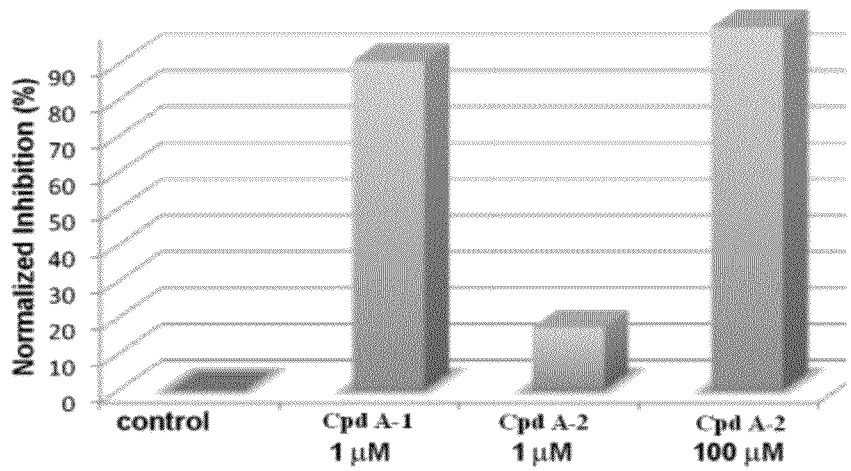

FIG. 2 is a bar graph showing the result of TLR4/MD-2 Pull Down Assay.

Figure 3A:
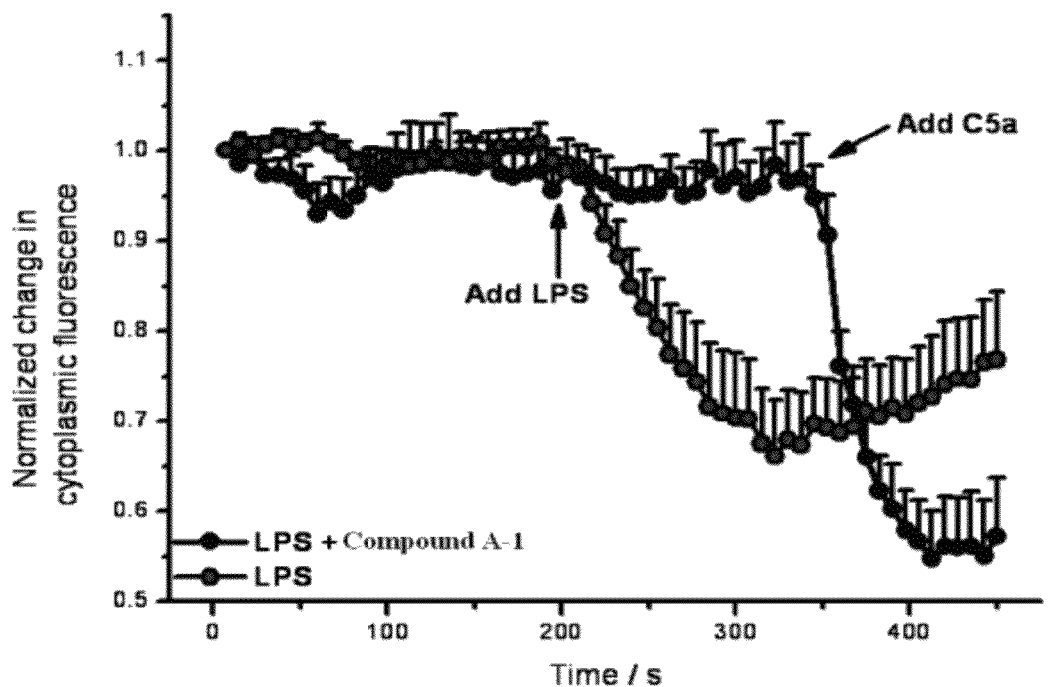
Figure 3B:
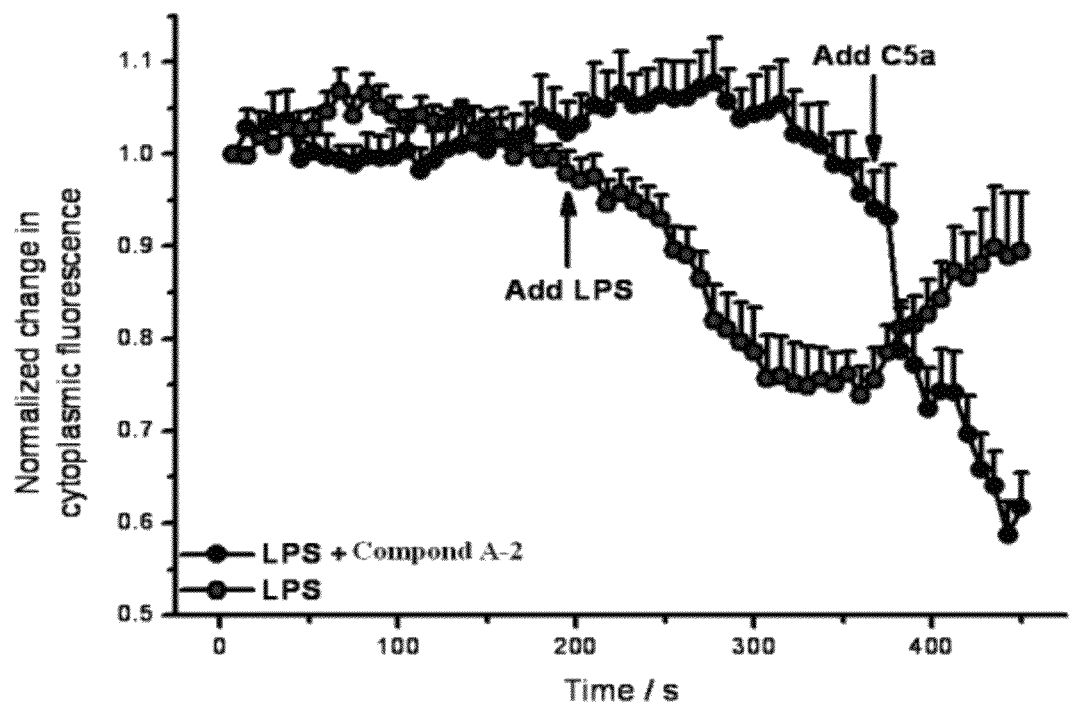

FIGS. 3A and 3B are graphs showing that Compound A-1 and Compound A-2, respectively, block LPS-induced TLR4 activation in macrophages.

Figure 4:
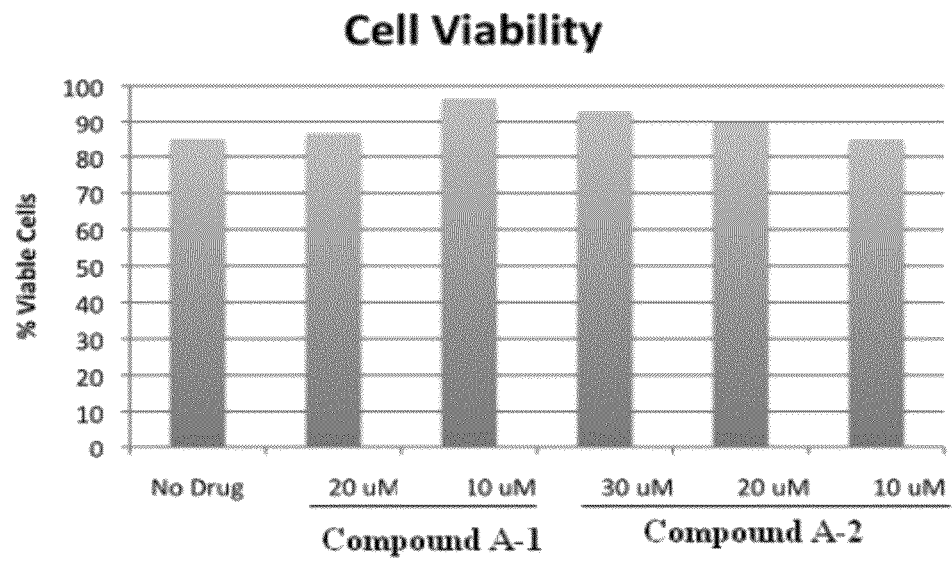

FIG. 4 is a bar graph of viability assay results that showed neither Compound A-1 nor Compound A-2 caused any significant cellular toxicity at these tested concentrations.

Figure 5A:
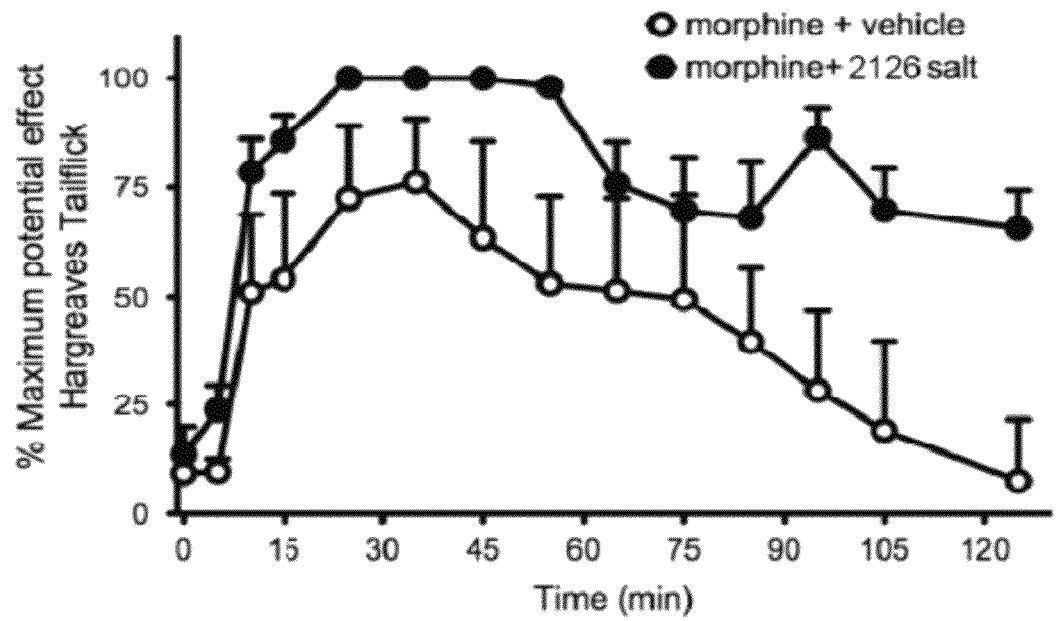
Figure 5B:
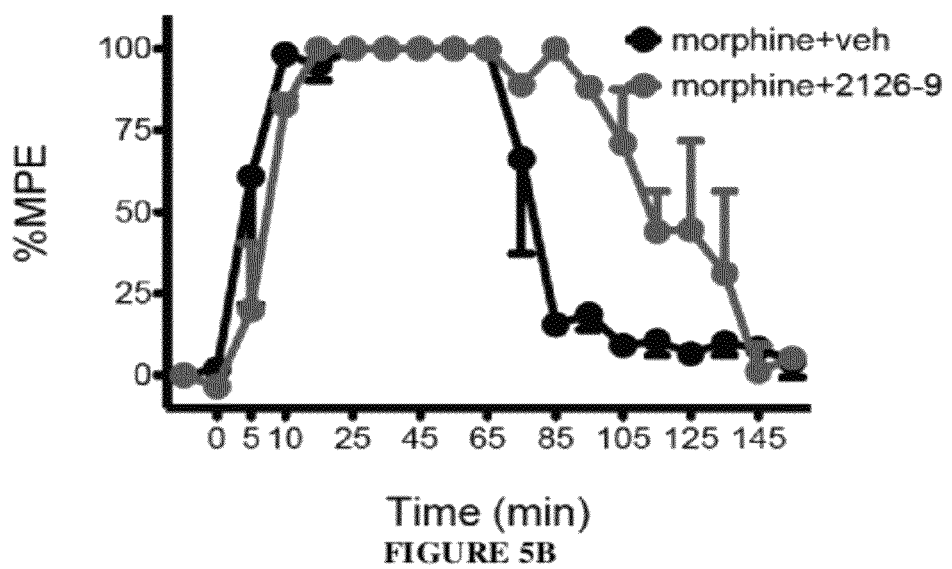
Figure 5C:
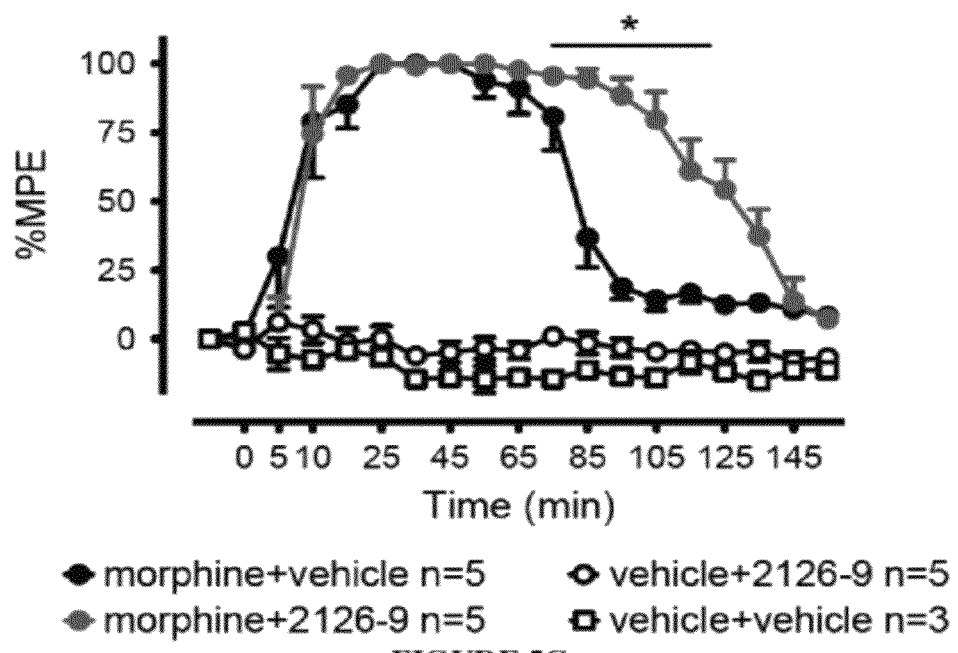

FIGS. 5A-5C show results of Hargreaves Test for some of the compounds of the invention.

DETAILED DESCRIPTION OF THE INVENTION

Definitions

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl group include, but are not limited to, methyl, ethyl, n-propyl, 2 propyl, tert-butyl, pentyl, and the like.

"Optionally-substituted alkyl" refers to an alkyl group as defined herein in which one or more hydrogen atom is optionally replaced with a substituent such as halide, hydroxyl, alkoxy, or other heteroatom substituent.

"Alkylene" refers to a saturated linear divalent hydrocarbon moiety of one to twelve, typically one to six, carbon atoms or a saturated branched divalent hydrocarbon moiety of three to twelve, typically three to six, carbon atoms. Exemplary alkyleme group include, but are not limited to, methylene, ethylene, propylene, butylene, pentylene, and the like.

"Alkenyl" refers to a linear monovalent hydrocarbon moiety of two to ten carbon atoms or a branched monovalent hydrocarbon moiety of three to ten carbon atoms, containing at least one double bond, e.g., ethenyl, propenyl, and the like.

"Alkenyl alkyl" refers to a moiety of the formula —$R^a$—$R^b$, where $R^a$ is alkylene and $R^b$ is alkenyl as defined herein.

"Alkoxy" refers to a moiety of the formula —$OR^n$, where $R^n$ is alkyl as defined herein.

"Alkoxyalkyl" refers to a moiety of the formula —$R^p$—O—$R^q$, where $R^p$ is alkylene and $R^q$ is alkyl as defined herein.

"Antagonist" refers to a compound or a composition that attenuates the effect of an agonist. The antagonist can bind reversibly or irreversibly to a region of the receptor in common with an agonist. Antagonist can also bind at a different site on the receptor or an associated ion channel. Moreover, the term "antagonist" also includes functional antagonist or physiological antagonist. Functional antagonist refers to a compound and/or compositions that reverses the effects of an agonist rather than acting at the same receptor, i.e., functional antagonist causes a response in the tissue or animal which opposes the action of an agonist. Examples include agents which have opposing effects on an intracellular second messenger, or, in an animal, on blood pressure. A functional antagonist can sometimes produce responses which closely mimic those of the pharmacological kind.

"Aryl" refers to a monovalent mono-, bi- or tricyclic aromatic hydrocarbon moiety of 6 to 15 ring atoms.

"Optionally-substituted aryl" refers to an aryl group as defined herein in which one or more aryl ring hydrogen is replaced with a non-hydrogen substituent such as halide, alkyl, cyano, hydroxy, alkoxy, etc. When two or more substituents are present in an aryl group, each substituent is independently selected.

"Aryloxy" and "arylthio" refer to a moiety of the formula —Z—$Ar^1$, where $Ar^1$ is aryl as defined herein and Z is O and S, respectively.

"Aralkyl" refers to a moiety of the formula —$R^xR^y$ where $R^x$ is an alkylene group and $R^y$ is an aryl group as defined herein. Exemplary aralkyl groups include, but are not limited to, benzyl, phenylethyl, 3-(3-chlorophenyl)-2-methylpentyl, and the like.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its minor image.

"Cycloalkyl" refers to a non-aromatic, typically saturated, monovalent mono-, bi- or tri-cyclic hydrocarbon moiety of three to twenty ring carbons. The cycloalkyl can be optionally substituted with one or more, typically one, two, or three, substituents within the ring structure. When two or more substituents are present in a cycloalkyl group, each substituent is independently selected. Exemplary cycloalkyl groups include, but are not limited to, cyclopropyl, cyclobutyl, cyclopentyl, norbornyl, adamantyl, cyclohexyl, cyclooctyl, etc.

"(Cycloalkyl)alkyl" refers to a moiety of the formula —$R^vR^w$ where $R^v$ is an alkylene group and $R^w$ is a cycloalkyl group as defined herein. Exemplary cycloalkylalkyl groups include, but are not limited to, cyclopropylmethyl, cyclohexylpropyl, 3-cyclohexyl-2-methylpropyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

"Hetero-substituted alkyl" refers to an alkyl group as defined herein that contains one or more heteroatoms such as N, O, or S. Such heteroatoms can be hydroxy, alkoxy, amino, mono- or di-alkyl amino, thiol, alkylthiol, etc.

"Hydroxyalkyl" refers to an alkyl group having one or more hydroxyl substituent.

"Enantiomeric excess" refers to the difference between the amount of enantiomers. The percentage of enantiomeric excess (% ee) can be calculated by subtracting the percentage of one enantiomer from the percentage of the other enantiomer. For example, if the % ee of (R)-enantiomer is 99% and % ee of (S)-enantiomer is 1%, the % ee of (R)-isomer is 99%-1% or 98%.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N, O—dimethylhydroxylamino, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, Protective Groups in Organic Synthesis, 3rd edition, John Wiley & Sons, New York, 1999, and Harrison and Harrison et al., Compendium of Synthetic Organic Methods, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any narrow and/or preferred, more preferred and most preferred definitions, if any.

The term "a derivative or an analog thereof" refers to those compounds that are derived from or having a similar core structure and retain all of the biological activity of the compound to which they are referred to. The term "all of the biological activity" refers to biological activities referred to herein when discussing the compound, e.g., TLR antagonistic property, etc.

"Chronic pain" refers to pain that persists longer than the temporal course of natural healing, associated with a particular type of injury or disease process.

"Nociceptive pain" refers to pain associated with the nerves which sense and respond to parts of the body which suffer from damage. Nociceptiv pain is caused by an injury or disease outside the nervous system. It is often an on-going dull ache or pressure, rather than the sharper, trauma-like pain more characteristic of neuropathic pain. They signal tissue irritation, impending injury, or actual injury. When activated, they transmit pain signals (via the peripheral nerves as well as the spinal cord) to the brain. The pain is typically well localized, constant, and often with an aching or throbbing quality. Visceral pain is the subtype of nociceptive pain that involves the internal organs. It tends to be episodic and poorly localized. Nociceptive pain is usually time limited, e.g., when the tissue damage heals, the pain typically resolves. (Arthritis is a notable exception in that it is not time limited.) Typically, nociceptive pain tends to respond well to treatment with opioids. Exemplary nociceptive pains include sprains, bone fractures, burns, bumps, bruises, inflammation (from an infection or arthritic disorder), obstructions, and myofascial pain (which may indicate abnormal muscle stresses).

Overview

Owing to the pain transmission capacity, neurons have been the primary intentional target of all pharmacotherapies developed to date. Generally, it is believed that opioids modulate pain solely by acting at neuronal opioid receptors and that opioid antagonists likewise exert their effects solely on neurons. Furthermore, it is conventionally believed that the detrimental (e.g., tolerance, hyperalgesia, dependence, and reward, etc.) and beneficial (e.g., analgesia, cough suppressant, etc.) actions of opioids are mediated via very similar and potentially inseparable mechanisms, reliant on neuronal opioid receptors.

In contrast, the present inventors have shown that the immunocompetent cells of the central nervous system (glia), their receptors, and their secreted signaling factors are involved in pain processing and opioid pharmacodynamics. In particular, glia have been shown to have a role in initiating and maintaining increased nociception in response to peripheral nerve injury. Recently, it has been suggested that glia can also modulate the analgesic actions of chronically administered opioids. Accordingly, some aspects of the invention provide pharmacological targeting (e.g., modulation) of glia to modulate (e.g., reduce or eliminate) pain and enhanced efficacy of opioids.

The present inventors also have shown that opioids cause direct glial activation in a non-classical opioid receptor fashion, via opioid-induced activation of a class of pattern recognition receptors termed Toll-like Receptors (TLRs). TLRs are significant mediators of neuropathic pain, opioid tolerance, opioid dependence, and opioid reward. Thus, in some instances antagonizing TLRs reverses neuropathic pain, and potentiates opioid and non-opioid analgesia. Also disclosed herein are the beneficial (e.g., classical neuronal opioid receptor mediated analgesia) and detrimental (e.g., glially mediated side effects) actions of analgesic compounds, such as opioids, and methods for modulating such.

Glial activation also contributes significantly to neuropathic pain and to the development of opioid tolerance, opioid dependence and opioid reward. Thus, attenuation of glial activation alleviates neuropathic pain and reduces the development of opioid tolerance, dependence and reward. It is believed that opioid-induced glial activation occurs via a non-opioid receptor due to non-stereoselective agonist activity. Accordingly, some aspect of the invention relates to attenuating glial activation by antagonizing or blocking TLR (e.g., TLR2, TLR4, other TLR that can bind to either opioid analgesics, non-opioid analgesics or endogenous danger signals known to be TLR agonists, or a combination thereof) or generally reducing glial activation. Reduction of glial activation reduces exaggerated pain states, enhances opioid analgesia, and reduces the development of opioid tolerance, dependence and reward.

Some of the other clinical conditions associated with TLR include, but are not limited to, gastrointestinal pathologies (e.g., colitis, inflammatory bowel disease, Crohn's disease, irritable bowel disease, and celiac disease), cardiovascular disease (e.g., inflammatory heart disease, vascular inflammation, myocardial ischemia/reperfusion injury, and atherosclerosis), diabetes [e.g., diabetes/insulin resistance, (killing of islet cells)], immune related conditions (e.g., allergy, asthma, eczema, auto-immune disorders including arthritis, lupus and glomerulonephritis), systemic pathologies (e.g., primary or secondary sepsis, transplant organ rejection, and liver toxicity), neurodegeneration (e.g., neurodegenerative disorders generally, including Alzheimer's, Parkinson's, dementia, Multiple Sclerosis, Huntington's disease, Amyotrophic lateral sclerosis, and aging), and other physiological function (e.g., induction of labor, fever, seizures, epilepsy, and epileptogenesis). Accordingly, some aspects of the invention provide methods for treating a clinical condition associated with agonism of TLR.

Conventionally, glia (astrocytes and microglia) were viewed as structural supports for neurons and important for maintaining central nervous system (CNS) homeostasis. Glia were long overlooked in pain research due to their lack of axons and their yet-to-be-discovered roles in cell-to-cell communication. The roles of CNS glia in providing immune surveillance, clearance of debris, and regulation of ionic and chemical composition of the extracellular space in the survival of the host are well known. However, a possible involvement of glia under varying pain states has only recently been investigated. One possible indication for a potential role of glia in pain regulation was an associative link between astrocyte activation and neuropathic pain, for example, drugs that blocked neuropathic pain also decreased glial activation.

Upon activation, the functions of microglia and astrocytes change in that they begin producing and releasing a variety of neuroexcitatory substances including traditional nociceptive modulators, such as reactive oxygen species, nitric oxide, prostaglandins, excitatory amino acids, growth factors, and proinflammatory cytokines, which was recently recognized. Principal among proinflammatory cytokines are interleukin (IL)-1, IL-6 and tumor necrosis factor-α. Without being bound by any theory, it is believed that spinal cord glia are one of the principal producers of these proinflammatory cytokines in the central nervous system. In fact, spinal glial activation and subsequent release of proinflammatory mediators are believed to be involved in initiating and maintaining diverse enhanced pain states including neuropathic pain.

There are numerous points along glial regulation of neuropathic pain where glia can be targeted to treat neuropathic pain. Traditional pain therapies have typically targeted transmission of the pain signal via neurons with limited success. However, merely treating the neuronal component of the pathology leaves the glial component unabated, still attempting to communicate to neurons to propagate pain signals. It is possible glia are activating neurons via different pathways/intracellular signaling cascades than modulated by drugs targeting neurons. Perhaps this explanation may elucidate the unfortunate lack of generalized success of current pain therapies.

One of the initial steps in the neuropathic pain pathway is believed to be activation of glia. A variety of glial activation signals have been identified. Signal(s) that initiates glial activation can vary depending on the insult delivered. Several mediators of glial activation are well characterized including neuronally-released fractalkine and traditional neuronal nociceptive modulators and transmitters, such as reactive oxygen species, nitric oxide, prostaglandins, excitatory amino acids, substance P, ATP, growth factors, and proinflammatory cytokines. In the majority of these cases, known receptor-mediated events have been characterized.

A variety of points in neuropathic pain can be targeted to treat neuropathic pain to which glia contribute. An activation signal or series of activation signals are required to activate glia. Activation of glia is often mediated via cell surface receptors that can be antagonized. The term "glial activation" refers to the state in which glia release proinflammatory mediators. This state (i.e., glial activation) can be modulated or attenuated thereby inhibiting various cellular events that block glial activation or its downstream consequences. An anti-inflammatory environment can also be produced which increases the threshold that an activation signal has to overcome to activate the cells.

Immune inflammatory mediators such as proinflammatory cytokines can be neutralized prior to reaching their intended receptor target (pre and/or post synaptic) by using soluble receptors (which exist endogenously), neutralizing antibodies, or compounds that decrease maturation of cytokines into their active form or increase the rate of cytokine degradation. The action of many glial inflammatory mediators on neurons (pre and/or post synaptic) can also be antagonized at neuronal receptor sites. There are myriads of currently employed neuronally targeted therapies that decrease the neuronal signaling of pain signals (pre and/or post synaptic).

Some aspects of the invention relate to modulating initiator and mediator of neuropathic pain that involve signals relayed by Toll-like Receptors (TLRs), such as TLR2, TLR4, other TLR that recognizes endogenous danger signals, or a combination thereof. TLRs are a family of approximately 10 single transmembrane receptors that recognize a diverse range of moieties or "patterns" on exogenous (e.g., lipopolysaccharide [LPS] of gram-negative bacteria such as *E. coli* and *Salmonella*) and endogenous (e.g., heat shock proteins and cell membrane components released from damaged cells) substances that are considered to be danger signals and hence warrant activation of the innate immune system aimed at defending the survival of the host. TLR4 has been extensively characterized, as it is the TLR that recognizes LPS. Binding of agonists to TLRs activate downstream intracellular signaling pathways (similar to IL-1 binding to its cognate receptor) resulting in a proinflammatory signal.

Some aspects of the invention modulate TLR2, TLR4, other TLR that can bind to either opioid analgesics, non-opioid analgesics or endogenous danger signals known to be TLR agonists, or a combination thereof. As disclosed herein, a wide variety of chemically diverse compounds can modulate TLR2, TLR4, other TLR as above, or a combination thereof. Without being bound by any theory, using TLR2 and TLR4 as exemplars, TLR2 and TLR4 are believed to be some (but not all) of the key TLRs for recognizing and responding to endogenous danger signals that are released by damaged, dying and dead neurons and other cells (host DNA and RNA, heat shock proteins, cell membrane components, etc) and more general aspects of tissue injury (plasma proteins, extracellular matrix degradation products, etc). The present inventors have shown that acute intrathecal administration of a selective TLR4 antagonist in normal rats suppresses well-established neuropathic pain induced by chronic constriction injury.

Peripheral nerve injury leads to protracted expression of heat shock proteins in proximal axons of damaged sensory neurons and degradation of presynaptic terminals. Nerve degeneration in the central nervous system occurs slowly, taking months to years. Therefore, it is clear that endogenous danger signals created as a result of nerve injury could produce perseverative activation of at least TLR2 and TLR4 and, thereby, a perseverative drive for maintaining neuropathic pain. Without being bound by any theory, it is believed that a parallel activation of at least TLR2 and TLR4 would be anticipated to occur in, and be causal to, spinal cord injury pain, post-stroke pain, multiple sclerosis pain and other pains of central nervous system origin. Accordingly, modulation of glial activation can be used to treat neuropathic pain.

Some aspects of the invention provide compounds and compositions that can modulate (e.g., antagonize) TLRs for neuropathic pain control. Given that TLR2, TLR4, and other TLRs can signal the presence of endogenous danger signals, some embodiments of the invention provide compounds and compositions that modulate TLR2, TLR4, other TLRs, or a combination thereof. In some embodiments, compounds and compositions of the invention are permeable to the blood-brain barrier.

The opioid receptor binds (−)-isomers of opioids selectively. The present inventors have found that a wide variety of compounds are capable of blocking LPS-induced activation of TLR4. Using a TLR4 stably transfected cell line (Invivogen) with a stable co-transfection of an NF-κB reporter gene (secreted embryonic alkaline phosphatase; SEAP) the present inventors have found a significant non-competitive antagonism of LPS activity at TLR4.

Compounds of the invention also reverses CCI-induced allodynia following a systemic administration. Such results indicate that blood brain barrier permeable small molecules can be used to antagonize TLR4 activity in vivo. In addition, TLR4 antagonism by small molecules can reverse CCI-induced allodynia. These data also show a role of TLR4 receptors in neuropathic pain. It is believed that opioid analgesia would be unaffected owing to the lack of opioid activity of the compounds of the invention. Without being bound by any theory, it is believed that compounds of the invention reverse neuropathic pain by antagonizing TLR4 receptors.

Compounds of the invention also reverse established allodynia and other neuropathic pain. Without being bound by any theory, it is believed that this activity is achieved via its actions as a TLR4 antagonist.

The mode of glial activation that results in enhanced pain can vary depending on the insult delivered. Thus, an effective treatment for neuropathic pain typically depends on which glial activating signal(s) are responsible for the pain pathway. A broader therapeutic approach is to inhibit or attenuate existing glial activation and/or products released by activated glia. In some instances, compounds of the invention reverse neuropathic pain and return the animal toward normal basal pain responsivity, rather than producing analgesia. Therefore, all of these treatments are anti-allodynic and/or anti-hyperalgesic, leaving basal nociception unaffected.

The inflammatory and pro-nociceptive mediators released by glia in their activated state are numerous. Therefore, clinically antagonizing or neutralizing each mediator has its limitations. However, in some instances proinflammatory cytokines appear to be one of the factors in glial enhancement of pain. In some cases, neutralizing the action of principal proinflammatory cytokines (e.g., IL-1, IL-6, tumor necrosis factor-α) or antagonizing their receptors has proven a successful strategy for preventing and reversing neuropathic pain.

It has been observed that there is a similarity between the glial activation observed in response to peripheral neuropathy and the glial activation following chronic opioid exposure. It has also been observed that opioid agonists activate TLR2, TLR4, other TLR, or a combination thereof and compounds of the invention non-stereoselectively block one or more of these receptors.

The present inventors have found that TLRs are responsible for both neuropathic pain and opioid-induced glial activation. Accordingly, some aspects of the invention provide methods for modulating neuropathic pain, opioid-induced glial activation, or a combination thereof by administering a TLR antagonist or a composition comprising the same. In some embodiments, the TLR antagonist does not significantly compromise the pain-suppressive effects of opioids agonists on neurons.

Since the discovery of morphine modulation of T cell function in 1979, a large amount of work has been focused on characterizing the influence that opioid exposure has on the functioning of the immune system in its traditional role of host defense. However, the impact that the activation status of immunocompetent cells has on opioid actions has only been recently studied. While modulation of peripheral immune cells function by opioids is important to understanding host defense, these cells are not as likely as glia to have a profound effect on opioid pharmacodynamics. The immunocompetent cells that mediate effects on opioid analgesia are typically the glia of the dorsal root ganglia, spinal cord and brain. Peripheral immune cells have been implicated in many TLR-mediated clinical diseases, such as Crohn's disease.

A causal link between opioid-induced glial activation and the development of opioid tolerance has recently been recognized. It is believed that following chronic morphine administration, tolerance and morphine-induced hyperalgesia are produced, at least in part, as a consequence of glial activation. One mechanism that has been proposed to account for such effects is via nitric oxide induced p38 MAPK activation, with downstream up regulation of proinflammatory cytokines. Interleukin-1, interleukin-6 and tumor necrosis factor, in turn, oppose morphine analgesia.

It is believed that morphine is acting not only at classical opioid receptors on nociceptive neurons but also as a glial activation signal producing the same, or at least a similar cascade of events that results in increased nociception. The sum of morphine's neuronal anti-nociceptive activity and its pro-nociceptive glial activation results in a net reduction in analgesia. Moreover, glial activation increases with prolonged opioid treatment and results in an increasing analgesic tolerance. Furthermore, opioid-induced glial activation contributes significantly to the atypical allodynia and hyperalgesia that results from chronic opioid administration. The present inventors have found that IL-1, as well as other proinflammatory cytokines, opposes morphine analgesia within minutes after either systemic or intrathecal administration.

The present inventors have observed similarity between neuropathy- and opioid-induced glial activations by using agents that reverse nerve injury-induced allodynia so as to define whether these same agents modulate morphine analgesia as well. The present inventors have discovered that agents that oppose neuropathic pain either by suppressing glial activation or by neutralizing or antagonizing proinflammatory glial products also oppose glial attenuation of both acute and chronic morphine analgesia. The efficacy of morphine can be potentiated by targeting opioid-induced glial activation or by neutralizing or antagonizing the action proinflammatory cytokines.

It is believed that the activation of glia is not mediated via a classical "neuronal-like" opioid receptor. The present inventors have discovered the involvement of a non-classical opioid receptor in glial activation using TLR antagonists, which possesses no classical opioid receptor activity, causes significant glial activation, allodynia and hyperalgesia, as well as upregulation of proinflammatory cytokine mRNA, protein and release. Some glia express classical opioid receptors. However, it is believed that the immunomodulation resulting from opioid exposure is not mediated by these receptors.

Some aspects of the invention provide methods for using TLR antagonists to potentiate (−)-opioid (e.g., morphine) analgesia, for example, by blocking (−)-opioid induced glial activation and consequent increase in anti-analgesic proinflammatory cytokines. In some embodiments, TLR antagonists significantly potentiated both acute and chronic (−)-opioid analgesia.

Without being bound by any theory, it is believed that (−)-opioids that are used in treating pain are agonists of TLR2, TLR4, other TLRs, or a combination thereof. For example, when several clinically employed (−)-opioids were tested, they were all found to be TLR4 agonists. These opioid TLR4 agonists included morphine, methadone, oxycodone, buprenorphine, fentanyl and pethadine/meperidine, amongst others.

In general, any TLR4 antagonists (e.g., oxcarbazepine, venlafaxine or other serotonin/norephinephrine reuptake inhibitor) can be used block TLR activation by drugs, by endogenous molecules (endogenous danger signals) and by foreign molecules (bacteria etc). In general, a TLR4 antagonist is useful in blocking TLR4 agonism by whatever means the TLR4 gets activated.

By targeting opioid-induced activation of glial TLRs, the present inventors were able to reduce or prevent this undesirable aspect of glial activation from progressing to opioid-induced tolerance, allodynia and hyperalgesia. The beneficial neuronally-induced opioid analgesia is unhindered by opioid-induced glial activation.

It is believed that at least TLR4 is responsible for initiating a component of opioid-induced glial activation that contributes significantly to the pro-nociceptive effects of opioid administration. Accordingly, some aspects of the invention provide methods for reducing pro-nociceptive effects of opioid administration by administering a TLR antagonist.

It has been observed that several non-selective immunosuppressive treatments ameliorate morphine withdrawal behaviors. In addition, glial involvement in pain enhancement during morphine withdrawal is blocked by IL-1 receptor antagonist or IL-10.

Co-administration of a TLR antagonist with an escalating dependence regimen of morphine significantly reduced naloxone precipitated withdrawal behaviors. Moreover, there was a corresponding reduction in glial activation in brain nuclei associated with opioid action.

In another experiment, a TLR antagonist was found to protect against previously established dependence and spontaneous withdrawal, as reflected by suppression of withdrawal induced spontaneous activity levels and weight loss. These data show that opioid-induced glial activation is involved in the development of morphine dependence and precipitation of withdrawal behaviors. Accordingly, some aspects of the invention provide methods for reducing opioid dependence, opioid withdrawal behaviors, or a combination thereof by administering a TLR antagonist. For example, the present inventors have observed that co-administration of a TLR antagonist significantly reduced withdrawal behaviors and attenuated morphine-induced weight loss.

As stated above, TLRs mediate the reinforcing and addictive actions of morphine. As such other aspects of the invention provide methods for increasing the beneficial actions, reducing the undesired effects, or a combination thereof of opioids. Such aspects of the invention often target glial activation. For example, it was observed that co-administration of a TLR antagonist resulted in a significant reduction in morphine reward.

Without being bound by any theory, it is believed that TLR-dependent glial activation results in neuropathic pain. Accordingly, some aspects of the invention provide methods for reducing neuropathic pain by modulating (e.g., reducing or preventing) TLR-dependent glial activation. One particular embodiment involves administering a TLR antagonist.

It is also believed that TLR-dependent opioid-induced glial activation results in opioid effects, such as reducing opioid (e.g., morphine) analgesia, producing opioid dependence and reward, and causing respiratory depression. Therefore, other aspects of the invention provide methods for reducing or preventing opioid effects, for example, reduction in opioid analgesia, dependence, reward, or a combination thereof. One particular embodiment involves administering a TLR antagonist.

The present inventors have also discovered that antagonizing TLRs or attenuating glial activation in neuropathic pain and during opioid exposure at least partially reverses allodynia and reduces unwanted opioid side effects, while maintaining opioid analgesic efficacy. The negative (i.e., undesired) side effects of opioids can be separated from the beneficial actions by, for example, targeting opioid-induced glial activation using blood brain barrier permeable pharmacotherapies such as TLR antagonists.

It is also believed that glial activation is at least partially responsible for the rewarding capacity of several abused compounds. Therefore, glial activation is a predictor for a patient's drug abuse liability. Examples of patient populations where this can pertain include HIV/AIDS, stress, and depression, etc. In all these cases, drug abuse is of considerable concern. Accordingly, some aspects of the invention provide methods for reducing or preventing drug abuse by administering a glial activation antagonist.

Compounds

Some aspects of the invention provide a compound selected from the group consisting of:

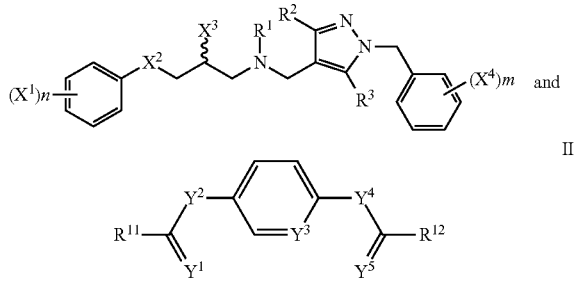

where
each of n and m is independently an integer from 0 to 5;
each $X^1$ is independently alkoxide, optionally-substituted alkyl, or alkenyl;
$X^2$ is O, $NR^a$, or S;
$X^3$ is —$OR^b$, —$SR^b$, or —$NR^b R^c$;
each $X^4$ is independently halide or alkoxide;
each of $R^1$, $R^2$ and $R^3$ is independently hydrogen, or alkyl;
each of $Y^1$ and $Y^5$ is independently O or S;
each of $Y^2$ and $Y^4$ is independently O, S, or $NR^c$;
$Y^3$ is CH or N;
each of $R^a$, $R^b$, $R^c$, $R^1$, $R^2$, and $R^3$ is independently hydrogen or alkyl;
$R^{11}$ is cycloalkyl or alkyl;
$R^{12}$ is alkyl, optionally-substituted aryl, or cycloalkyl.

In some embodiments, the compound is of the formula:

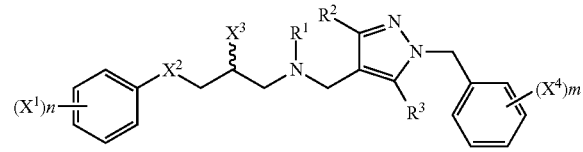

where
each of m and n is independently an integer of 0-5; typically each of m and n is independently an integer of 0-4; often each of m and n is independently an integer of 0-2; and
$X^1$, $X^2$, $X^3$, $X^4$, $R^1$, $R^2$, and $R^3$ are those defined in herein.

Within these embodiments, in some instances $X^2$ is O, Still in other instances, $X^3$ is —OH. Yet in other instances, $R^1$, $R^2$ and $R^3$ are alkyl. Typically, $R^1$, $R^2$, and $R^3$ are methyl. Yet in other instances, $X^1$ is alkoxide, hetero-substituted alkyl or alkenylalkyl. Often $X^1$ is methoxide, methoxyethyl, or allyl. Still in other instances, $X^4$ is alkoxide, Cl, or F. Typically, $X^4$ is methoxide or Cl.

In other embodiments, the compound is of the formula:

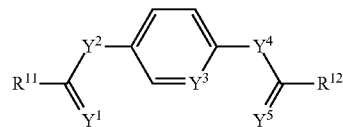

where
$Y^1$ and $Y^5$ are O; and
$R^{11}$, $R^{12}$, $Y^2$, $Y^3$, and $Y^4$ are those defined herein.

Within these embodiments, in some instances $Y^2$ is $NR^c$. Typically, $R^c$ is hydrogen. Yet in other instances, $Y^4$ is O or NH. Still in other instances, $R^{11}$ is adamantyl, n-butyl, isobutyl, n-pentyl, or 1-ethylpropyl. In other instances, $R^{12}$ is alkyl, adamantyl, cyclohexyl, or optionally substituted phenyl. Often $R^{12}$ is iso-butyl, n-butyl, sec-butyl, tert-butyl, n-pentyl, cyclohexyl, adamantyl, phenyl, methoxyphenyl, or chlorophenyl.

It should be recognized that combinations of various embodiments described herein form other embodiments. In this manner, a variety of compounds, compositions, and methods are embodied within the invention.

Other aspects of the invention provide a composition comprising a compound of Formula I and/or II, or a pharmaceutically acceptable salt or a pro-drug thereof.

Synthesis

Compounds of the invention can be readily prepared from available starting materials. Various substituents on the compounds of the invention can be present in the starting compounds, added to any one of the intermediates or added after formation of the final products by known methods of substitution or conversion reactions. For example, nitro groups can be added by nitration and the nitro group can be converted to other groups, such as amino by reduction, and halogen by diazotization of the amino group and replacement of the diazo group with halogen or simply by halogenation reaction. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, 3rd ed., John Wiley & Sons, New York, 1999, and references cited therein, all of which are incorporated herein by reference in their entirety.

Since the compounds of the invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent on the ring involved.

In some instances, a racemic mixture of compounds of the invention can be prepared and the desired (+)- or (−)-isomer can be resolved or separated (i.e., enantiomerically enriched) using any of the variety of chiral resolution methods known to one skilled in the art. Such resolution methods are described, for example, in the four volume compendium *Optical Resolution Procedures for Chemical Compounds: Optical Resolution Information Center*, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety.

In some resolution methods, a racemic mixture is converted to a mixture of diasteromers by attachment, either chemically or enzymatically, of a relatively enantiomerically pure moiety. Unlike enantiomers, most diastereomers have different physical properties, e.g., solubility, boiling point, affinity (e.g., to chromatography columns and enzymes), and the like. These different physical properties can be used to separate one diastereoisomer from another, for example, by fractional crystallization, distillation, chromatography, kinetic resolution using an enzyme, and the like.

Alternatively, the compound can be synthesized enantioselectively starting from enantiomerically pure or enriched starting material.

When the compound of the present invention contains an olefin moiety and such olefin moiety can be either cis- or trans-configuration, the compound can be synthesized to produce cis- or trans-olefin, selectively, as the predominant product. Alternatively, the compound containing an olefin moiety can be produced as a mixture of cis- and trans-olefins and separated using known procedures, for example, by chromatography as described in W. K. Chan, et al., J. Am. Chem. Soc., 1974, 96, 3642, which is incorporated herein in its entirety.

The compounds of the invention form salts with acids when a basic amino function is present and salts with bases when an acid function, e.g., carboxylic acid or phosphonic acid, is present. All such salts are useful in the isolation and/or purification of the new products. Of particular value are the pharmaceutically acceptable salts with both acids and bases. Suitable acids include, for example, hydrochloric, oxalic, sulfuric, nitric, benzenesulfonic, toluenesulfonic, acetic, maleic, tartaric and the like which are pharmaceutically acceptable. Basic salts for pharmaceutical use include Na, K, Ca and Mg salts.

Methods for producing many of the compounds of the invention are readily available from various journal articles, which can be readily obtained by, for example, searching chemical abstract services data base, e.g., CAS online.

Pharmaceutical Compositions

The compounds of the invention can be administered to a patient to achieve a desired physiological effect. Typically the patient is a mammal, often human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal, and inhalation (e.g., via insufflation and aerosol); intraperitoneal; rectal systemic, and central (e.g., intrathecal, such as into the cerebrospinal fluid around the spinal cord, and intracerebral into brain or CSF of the brain).

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Preferred compositions or preparations according to the present invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of the invention can be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

It is believed that glia are activated by opiates (e.g., morphine, methadone, meperidine and oxycodone) and that this opioid-induced glial response suppresses opioid analgesia, contributing to the development of opioid tolerance and dependence. The present inventors have discovered that opioid-induced glial activation is regulated by the toll-like receptor 4 (TLR4) signaling pathway. TLR4 is a membrane spanning receptor that functions in complex with its accessory protein myeloid differentiation factor 2 (MD-2). This discovery of opioids interacting with TLR4 by the present inventors led to developing compounds that can improve current opioid-based pain management therapies.

TLR4 is a surface receptor of the TLR protein family, a group of type I integral membrane glycoproteins that include more than 11 homologous members. Stimulation of different TLRs induces distinct patterns of gene expression, which not only leads to the activation of innate immunity but also instructs the development of antigen-specific acquired immunity. It is believed that TLR4 detects lipopolysaccharide (LPS, a classic TLR4 agonist and a component of gram-negative bacterial cell walls) and is thus important in the activation of the innate immune system. Within the central nervous system (CNS), it is believed that TLR4 is expressed primarily by glia (predominantly microglia but also some astrocytes) but not by neurons. These glia are immunocompetent cells important in CNS innate immune responses. The functional distinction between neurons and glia indicates it is possible to selectively target glia without affecting neurons. This selectivity allowed methods for potentiating the analgesic effects of morphine. In some embodiments, by suppressing the glia-activating side-effects of morphine, but sustaining the analgesic effect on neurons, it is possible to improve the activity of morphine while simultaneously inhibiting pathways which contribute to the development of opioid tolerance and addiction.

The TLR4/MD-2 interaction is one of the attractive therapeutic targets because the interaction is part of the TLR4 signaling pathway. Furthermore, MD-2 primarily interacts with TLR4 among the TLR family proteins. Such findings allow selectivity and specificity to the small-molecule modulators (e.g., inhibitors). In some embodiments, a chemical biology approach was used to establish the TLR4/MD-2 complex as a valid target for drug discovery by using two small-molecule probes targeting the TLR-4/MD-2 interface: one targeting each protein binding partner. Both in vitro and in vivo studies showed the efficacy of the molecules. These results show a new strategy to abolish opioid-induced glial activation. Such strategy also provides tools to investigate the development of opioid dependence and tolerance.

In order to identify small-molecule probes for investigating TLR4-mediated glial activation, the present inventors used high-resolution X-ray structures of the TLR4/MD-2 complex. A high-throughput in silico screening methodology was developed to identify selective inhibitors of the TLR4 signaling pathway. The methodology was applied to both proteins in the complex, targeting the protein-protein interface in order to both validate the strategy and maximize the chances of identifying useful chemical probes. Starting from the high-resolution structure of MD-2 (PDB ID 2E56, resolution 2.00 Å), the protein was first relaxed with a molecular dynamics run in order to establish each protein target, represented using various protein conformations. The structure of TLR4 was taken from the complex of the human TLR4 with the lymphocyte antigen 96 (PDB ID 2Z65, resolution 2.70 Å).

Figure 1:
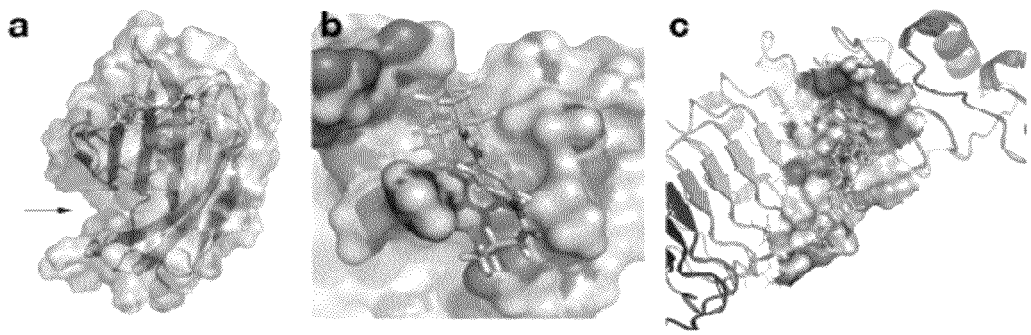
FIGS. 1A-1C show results of the molecular-docking experiments of (a, b) Compound A-2 binding to MD-2; (a) Global view of the compound A-2/human MD-2 complex, showing that compound A-2 recognizes an allosteric site that is different from the LPS-binding site (arrow indicated) on the MD-2 surface. (b) Close-up view showing that compound A-2 recognizes the pocket with high spatial complementarity.

The structures of ligands for virtual screening were taken from ENAMINE screening collection library that contains 1 million drug-like small molecule agents. The library was first clustered using Jarvis-Patrick algorithm implemented in QUANTUM. The measure of dissimilarity ("distance") between the molecules was determined by Tanimoto similarity calculated with Daylight fingerprints of the molecules. Free Energy Perturbation molecular dynamics run for the whole protein-ligand complex in aqueous environment was performed using continuous solvation model developed by the present inventors. This method has been proven to be highly accurate in calculating the free energy of a polar liquid. The modeling led to a focused library of roughly 10 k cluster representatives of appropriate molecular weight. All the selected compounds were extracted from ENAMINE-supplied sdf files, processed through the QUANTUM structure recovery and typization software components in a batch mode and prepared for subsequent docking. This output, together with the best cluster centroids, was selected for subsequent molecular dynamics simulations. In addition, a "fingerprint"

of the identified hits was profiled by docking them to an original panel of proteins representing the whole human proteome (ca. 500 representative proteins selected from various protein families) and collected $IC_{50}$ data on every protein/small-molecule and protein/protein complex out of this panel. By doing these additional dockings, the likelihood of identifying highly selective and specific inhibitors for the two proteins was increased. Modeling showed Compound A-1 binds to TLR4 with calculated $IC_{50}$ values<10 μM and Compound A-2 was a potent MD-2 antagonist. See FIG. 1.

These compounds were synthesized as shown in Schemes 1 and 2. Compound A-2 was prepared in two steps by iterative acylations of 1,4-diphenylenediamine (2-2). Synthesis of Compound A-1 was achieved by alkylation of the pyrazole (1-3), followed by a Mannich-like reaction to produce the tetrasubstituted pyrazole derivative (1-5). Finally, epoxide opening of compound 1-2 with the amino functionality of compound 1-5 provided Compound A-1.

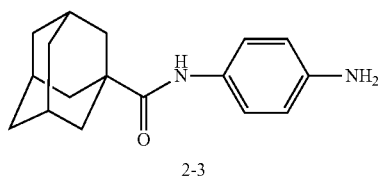

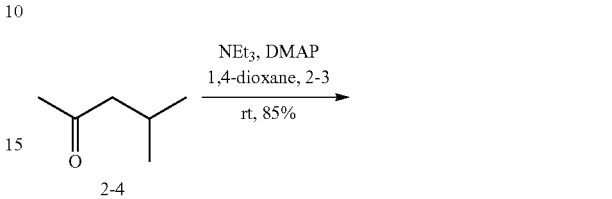

Scheme 1

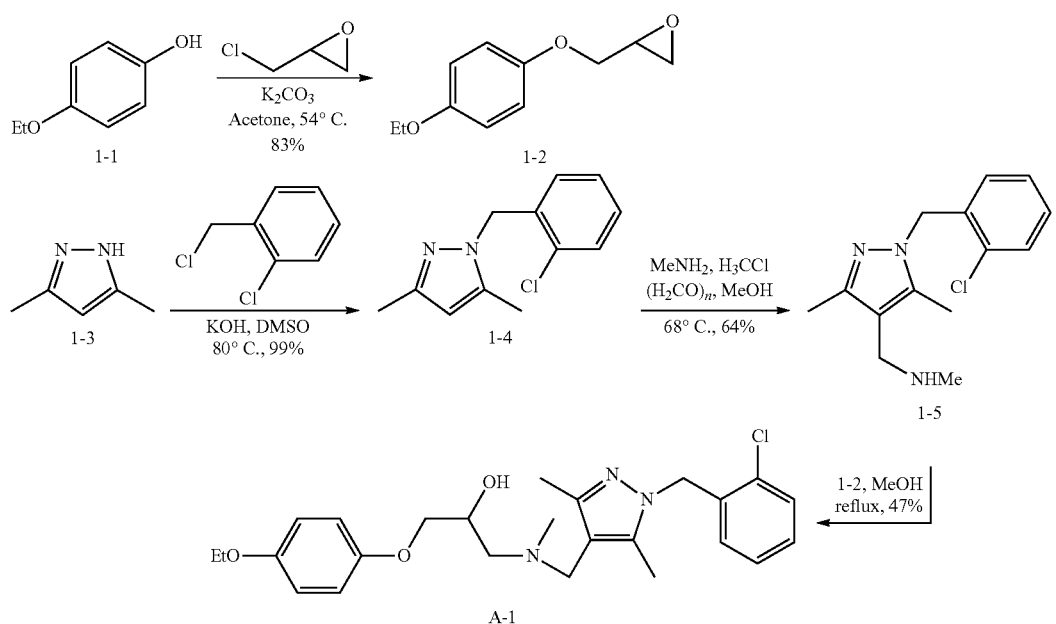

Scheme 2

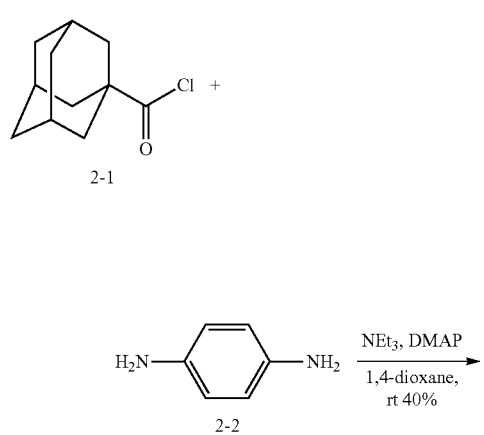

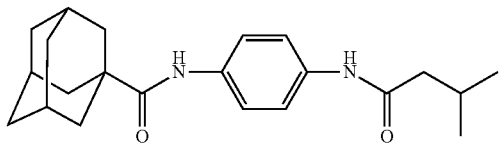

These compounds were also evaluated for inhibition of the TLR4 signaling pathway in vitro and in vivo. A pull-down assay showed that Compounds A-1 and A-2 disrupted the TLR4/MD-2 interaction. HeLa cells were co-transfected with expression vectors for FLAG-sTLR4 and MD-2-FLAG-His. The MD-2/TLR4 protein complex was purified from the culture supernatants using nickel resin, separated by SDS-PAGE and detected by immunoblotting against the FLAG tag. Incubating the MD-2/TLR-4 complex in the presence of 0.1-100 μM of Compound A-2 substantially eliminated abolished TLR4 binding to MD2, quantified by visualization of the FLAG tags by Western blotting. Compound A-1 exhibited a similar effect (FIG. 2).

Monitoring the Akt1 signaling showed that both Compound A-1 and Compound A-2 blocked TLR4-signaling in a rat macrophage cell line (RAW 264.7). Lipopolysaccharide (LPS)-induced TLR4 activation initiates the phosphoinositide 3-kinase (PI3K) cascade, triggering translocation of Akt1 to the plasma membrane in murine macrophages. RAW 264.7 cells transfected with an Akt1-GFP reporter13 were treated with drug then activated with LPS. In the absence of LPS, Akt1-GFP was uniformly diffused throughout the cytosol as observed by fluorescence microscopy. Addition of LPS (2 ng/ml) caused a rapid translocation of Akt1-GFP to the plasma membrane, lowering the Akt1-GFP concentration in the cytosol. Doses of Compound A-1 as low as 2 µM and Compound A-2 as low as 200 nM substantially abolished LPS-induced activation of the signaling pathway. See FIGS. 3A and 3B.

After addition of LPS, these cells showed a very similar activation profile to untreated cells. FIGS. 3A and 3B. A small dose of chemotactic peptide C5a (25 ng/mL) that stimulates PI3K15 was able to rescue the Akt signaling inhibited by either compound. Global translocation of Akt1-GFP to the plasma membrane was observed, confirming that these cells retained normal Akt signaling transduction functions. Akt1 is directly downstream of TLR4 in the signal transduction pathway. Therefore, these data indicate that both Compound A-1 and Compound A-2 block TLR4-mediated signaling by directly interacting with the TLR4/MD-2 complex. Murine macrophages express a variety of TLRs and immune receptors. Inhibiting LPS-induced agonism of TLR4 indicates that both antagonists are specific for the TLR4 pathway over other TLRs. The activity of Compound A-1 was further confirmed in an established TLR4 assay in HEK293 cells, where a secreted alkaline phosphatase reporter gene is located downstream from the NF-κB promoter. Compound A-1 was effective at blocking the downstream proinflammatory effectors of TLR4 in a dose-dependent manner. Moreover, neither Compound A-1 nor Compound A-2 showed any significant cellular toxicity. See FIG. 4.

An established animal model was used to test whether the TLR4 signaling antagonists were able to potentiate the analgesic effect of morphine in vivo. The Hargreaves test was used to measure the time taken to observe radiant heat-induced withdrawal responses by the hindpaws and tails of unrestrained rats.

Before drug administration, two readings were recorded for each site with baseline latencies of 5-6 seconds. Following these pre-drug baseline measurements, drugs were injected intrathecally (into the cerebrospinal fluid space surrounding the lumbosacral spinal cord) and the rats' responses to radiant heat re-assessed across a two hour time course. Injection of either Compound A-1 or Compound A-2 alone produced no detectable behavioral effects (e.g., no self-directed biting or struggling, no vocalization, nor other sign of distress). While the small molecule probes had no effect on pain responsivity in the absence of co-administered morphine, they significantly potentiated the analgesic effects of morphine such that the rats exhibited the maximal analgesia recordable on the test across the two hour time course (heat automatically terminated at 10 seconds to avoid tissue injury).

A chemical biological approach to studying the field of neurobiology has provided a useful tool in understanding of the mechanisms of glial activation. Using in silico high-throughput screening, the present inventors have indentified selective and specific inhibitors of the TLR4/MD-2 interaction. Compound A-2 targeted MD-2 and Compound A-1 targeted TLR4. It was also demonstrated that both of these compounds potentiate the analgesic effects of morphine. The TLR4/MD-2 interaction is a suitable molecular target for the regulation of opioid-induced glial activation. Some aspects of the invention also provide a therapeutic strategy for suppressing opioid tolerance and dependence.

Molecular Modeling and Prediction of Physical-Chemical Parameters

The virtual screening procedure included two stages: docking to a static protein model and refinement using dynamic protein model. Docking to a static and dynamic protein models were performed using Quantum software utilities. Docking to a static protein model included identification of the ligand position in the binding pocket with the minimal binding energy, and estimation of the binding energy. In molecular dynamics study the calculated protein-ligand binding energy were refined with regard to the protein flexibility. Refinement procedure used was a complete Free Energy Perturbation molecular dynamics run for the whole protein-ligand complex in aqueous environment. Thus, it regards both protein and ligand flexibility.

Chemical Synthesis

All reactions were run in oven-dried or flame-dried glassware under a dry nitrogen or argon atmosphere. Methanol was distilled by simple distillation and stored over 4 Å molecular sieves. Acetone was distilled before use. Methylamine.HCl salt was dried under high-vac overnight using $P_2O_5$ as a decadent. All other reagents and solvents were used as received from the supplier. Flash chromatography was performed using 32-64 µm silica gel. $^1$H NMR spectra were recorded at 300 MHz, 400 MHz, or 500 MHz in $CDCl_3$ using residual $CHCl_3$ (7.26 ppm) as the internal standard. $^{13}$C NMR spectra were recorded at 75 MHz in $CDCl_3$ using residual $CHCl_3$ (77.23 ppm) as an internal reference. Exact mass was determined using electrospray ionization.

2-((4-ethoxyphenoxy)methyl)oxirane

4-Ethoxyphenol (0.25 g, 1.81 mmol), anhydrous potassium carbonate (0.50 g, 3.62 mmol) and epichlorohydrin (0.57 ml, 7.24 mmol) were added to acetone (4.52 ml) and the resulting heterogeneous solution was refluxed for 16 hrs. The mixture was cooled to room temperature, filtered through a pad of celite and the filtrate was concentrated under reduced pressure. The resulting oil was dissolved in toluene (20 mL), washed sequentially with water (15 mL), 5% aqueous NaOH (20 mL) and water again (20 mL). The organic layer was dried with $MgSO_4$ and concentrated under reduced pressure to yield 0.292 g (83%) of 2-((4-ethoxyphenoxy)methyl)oxirane as a white solid (mp=41° C.). $^1$H NMR (400 MHz, $CDCl_3$) δ 6.91-6.77 (m, 4H), 4.17 (dd, J=11.0, 3.2, 1H), 3.98 (q, J=7.0, 2H), 3.91 (dd, J=11.0, 5.6, 1H), 3.34 (m, 1H), 2.90 (dd, J=4.9, 4.1, 1H), 2.75 (dd, J=5.0, 2.7, 1H), 1.39 (t, J=6.98, 3H). $^{13}$C NMR (75 MHz, $CDCl_3$) δ 153.72, 152.78, 115.90, 115.90, 115.59, 115.59, 69.71, 64.18, 50.49, 44.98, 15.15. HRMS (m/z): [MNa]$^+$ calc. for $C_{11}H_{14}O_3Na^+$, 217.08. found 217.0826.

1-(2-chlorobenzyl)-3,5-dimethyl-1H-pyrazole

Powdered potassium hydroxide (1.751 g, 31.2 mmol) was added to a solution of 3,5-dimethylpyrazole (2 g, 20.81 mmol) in anhydrous DMSO (10.40 ml) and the resulting heterogeneous solution was stirred for 1.5 hr at 80° C. before being cooled to room temperature. 2-Chloro benzylchloride (2.64 ml, 20.81 mmol) was then added in 6 M DMSO over 15 min, and the solution was stirred for a further 1.5 hrs. Upon completion as observed by TLC, the reaction was poured over water and the resulting aqueous phase was extracted with two 20 mL portions of CHCl$_3$. The combined organic layers were washed with 100 mL of water, dried with anhydrous MgSO$_4$ and concentrated under reduced pressure to yield 4.55 g (99%) of 1-(2-chlorobenzyl)-3,5-dimethyl-1H-pyrazole as a clear liquid. $^1$H NMR (300 MHz, CDCl$_3$) δ 7.41-7.31 (m, 1H), 7.24-7.09 (m, 2H), 6.59-6.50 (m, 1H), 5.90 (s, 1H), 5.31 (s, 2H), 2.26 (s, 3H), 2.15 (s, 3H). $^{13}$C NMR (75 MHz, CDCl$_3$) δ 148.32, 139.96, 135.46, 131.96, 129.42, 128.76, 127.72, 127.48, 105.84, 50.12, 13.80, 11.15. HRMS (m/z): [MNa]$^+$ calc for C$_{12}$H$_{13}$ClN$_2$Na$^+$ 243.07. found 243.0651.

1-(1-(2-chlorobenzyl)-3,5-dimethyl-1H-pyrazol-4-yl)-N-methylmethanamine

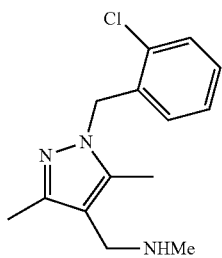 [SMILES: CNCc1c(C)nn(Cc2ccccc2Cl)c1C]

A solution of 1-(2-chlorobenzyl)-3,5-dimethyl-1H-pyrazole (1.00 g, 4.53 mmol), paraformaldehyde (0.82 g, 27.20 mmol) and methylamine.HCl (0.92 g, 13.59 mmol) dissolved in methanol (9.06 ml) was stirred at 60° C. for 24 hrs. The mixture was cooled to room temperature and quenched with aqueous NaHCO$_3$ (15 mL). The aqueous layer was extracted 3 times with ether (15 mL) and the combined organic layers washed with brine (30 mL). The organic layer was dried with MgSO$_4$ and concentrated under reduced pressure. The resulting yellow oil was purified using flash column chromatography with 1:4:0.01 ethyl acetate:hexanes:triethylamine as eluting solvent yielding 0.73 g (62%) of 1-(1-(2-chlorobenzyl)-3,5-dimethyl-1H-pyrazol-4-yl)-N-methylmethanamine as a clear oil. $^1$H NMR (300 MHz, CDCl$_3$) δ 7.40-7.31 (m, 1H), 7.23-7.08 (m, 2H), 6.54-6.43 (m, 1H), 5.32 (s, 2H), 3.31 (s, 2H), 2.91 (s, 1H), 2.25 (s, 3H), 2.16 (s, 3H), 2.12 (s, 3H). $^{13}$C NMR (75 MHz, CDCl$_3$) δ 148.12, 138.48, 135.57, 131.94, 129.42, 128.72, 127.61, 127.41, 114.38, 50.24, 49.08, 40.68, 12.36, 9.75. HRMS (m/z): [MH]$^+$ calc for C$_{14}$H$_{18}$ClN$_3$, 264.13. found 264.1253.

1-(((1-(2-chlorobenzyl)-3,5-dimethyl-1H-pyrazol-4-yl)methyl)(methyl)amino)-3-(4-ethoxyphenoxy)propan-2-ol

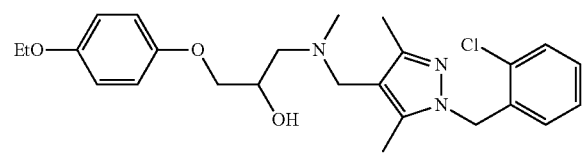 [SMILES: CCOc1ccc(OCC(O)CN(C)Cc2c(C)nn(Cc3ccccc3Cl)c2C)cc1]

2-((4-Ethoxyphenoxy)methyl)oxirane (0.06 g, 0.32 mmol) and 1-(1-(2-chlorobenzyl)-3,5-dimethyl-1H-pyrazol-4-yl)-N-methylmethanamine (0.10 g, 0.38 mmol) were dissolved in methanol (0.32 ml), warmed to 68° C. and stirred until the oxirane was consumed as observed by TLC. The solution was cooled to room temperature and the solvent removed under reduced pressure. The resulting oil was purified using flash column chromatography with 1:2:0.01 ethyl acetate:hexanes:triethylamine as the eluting solvent to yield 0.09 g (63%) of 1-(((1-(2-chlorobenzyl)-3,5-dimethyl-1H-pyrazol-4-yl)methyl)(methyl)amino)-3-(4-ethoxyphenoxy)propan-2-ol as a clear liquid. $^1$H NMR (500 MHz, CDCl$_3$) δ 7.35 (dd, J=7.8, 1.2, 1H), 7.17 (td, J=7.7, 1.3, 1H), 7.12 (td, J=7.5, 1.2, 1H), 6.85-6.79 (m, 4H), 6.48 (dd, J=7.6, 0.9, 1H), 5.28 (s, 2H), 4.12-4.04 (m, 1H), 3.97 (q, J=7.0, 2H), 3.90 (d, J=4.9, 2H), 3.47 (d, J=13.2, 1H), 3.34-3.29 (m, 1H), 2.60 (dd, J=12.2, 9.7, 1H), 2.48 (dq, J=12.2, 3.9, 1H), 2.26 (s, 3H), 2.24 (s, 3H), 2.11 (s, 3H), 1.38 (t, J=9.1, 3H). $^{13}$C NMR (75 MHz, CDCl$_3$) δ 153.47, 153.04, 148.04, 138.67, 135.31, 131.92, 129.43, 128.79, 127.58, 127.50, 115.63, 115.63, 115.53, 115.53, 113.71, 71.25, 66.37, 64.14, 59.51, 51.70, 50.28, 42.09, 15.13, 12.36, 9.82. HRMS (m/z): [MNa]$^+$ calc for C$_{25}$H$_{32}$ClN$_3$O$_3$Na$^+$, 480.20. found 480.2030.

Compound A-2

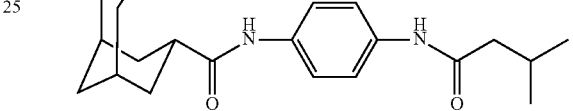

1-Adamantanecarbonyl chloride (238 mg, 1.20 mmol) was added to a mixture of 1,4-diphenylenediamine (108 mg, 1.0 mmol), triethylamine (202 mg, 2.00 mmol), DMAP (6 mg, 0.05 mmol) and 1,4-dioxane (4.0 ml) at rt. After stirring for 12 hours, half of the reaction solvent was evaporated and the subsequent solution was subjected to column chromatography with EtOAc as the eluent. The intermediate was obtained as a colorless powder; yield 113 mg, 40%. Isovaleryl chloride (14 mg, 0.10 mmol) was added to a solution of the intermediate (27 mg, 0.10 mmol), triethylamine (20 mg, 0.20 mmol), DMAP (1.2 mg, 0.010 mmol) and 1,4-dioxane (1.0 ml) at rt. After stirring for 12 hours, the reaction mixture was subject to column chromatography (1:1 EtOAc-Hexanes). Compound A-2 was obtained as colorless powder; yield 30 mg, 85%.

Other Compounds

Some of the representative compounds that were prepared and tested are listed below (some of the salts and enantiomerically enriched isomers were also prepared but are not shown separately):

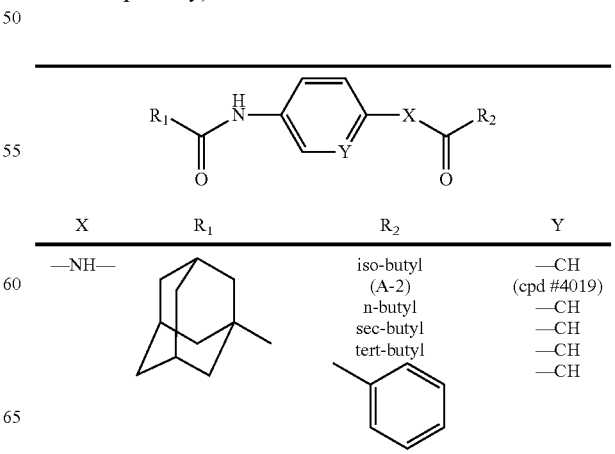

| X | R$_1$ | R$_2$ | Y |
|---|---|---|---|
| —NH— | adamantyl | iso-butyl (A-2) | —CH (cpd #4019) |
| | | n-butyl | —CH |
| | | sec-butyl | —CH |
| | | tert-butyl | —CH |
| | | phenyl | —CH |

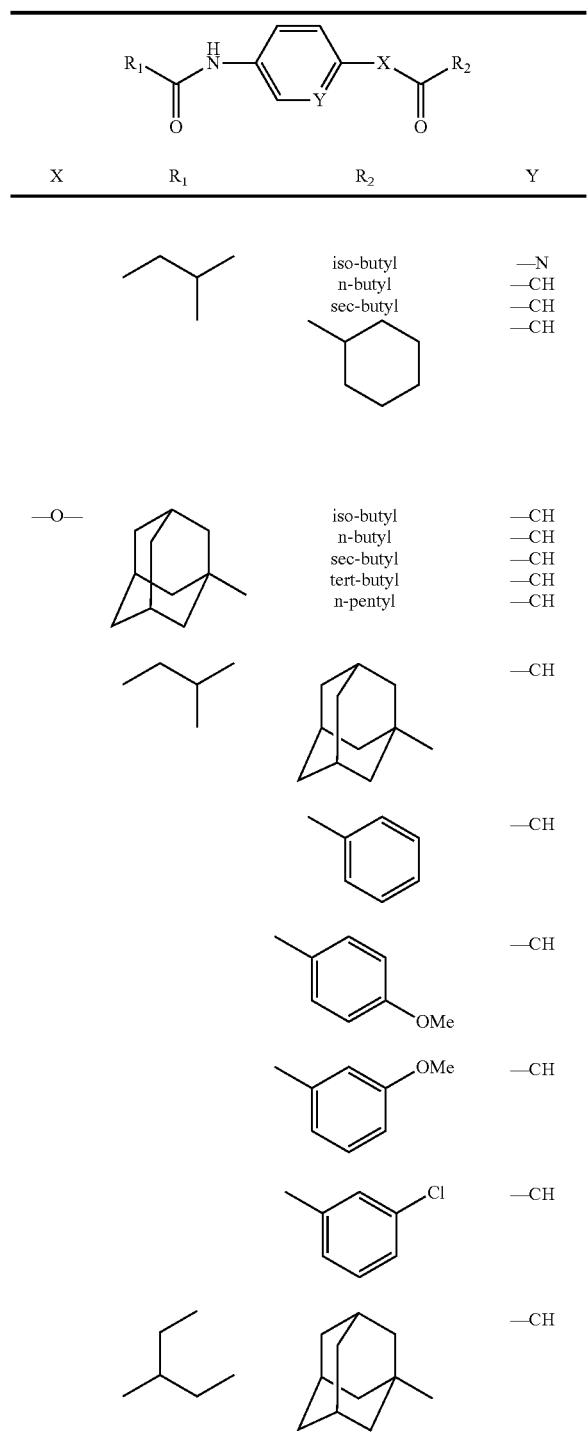
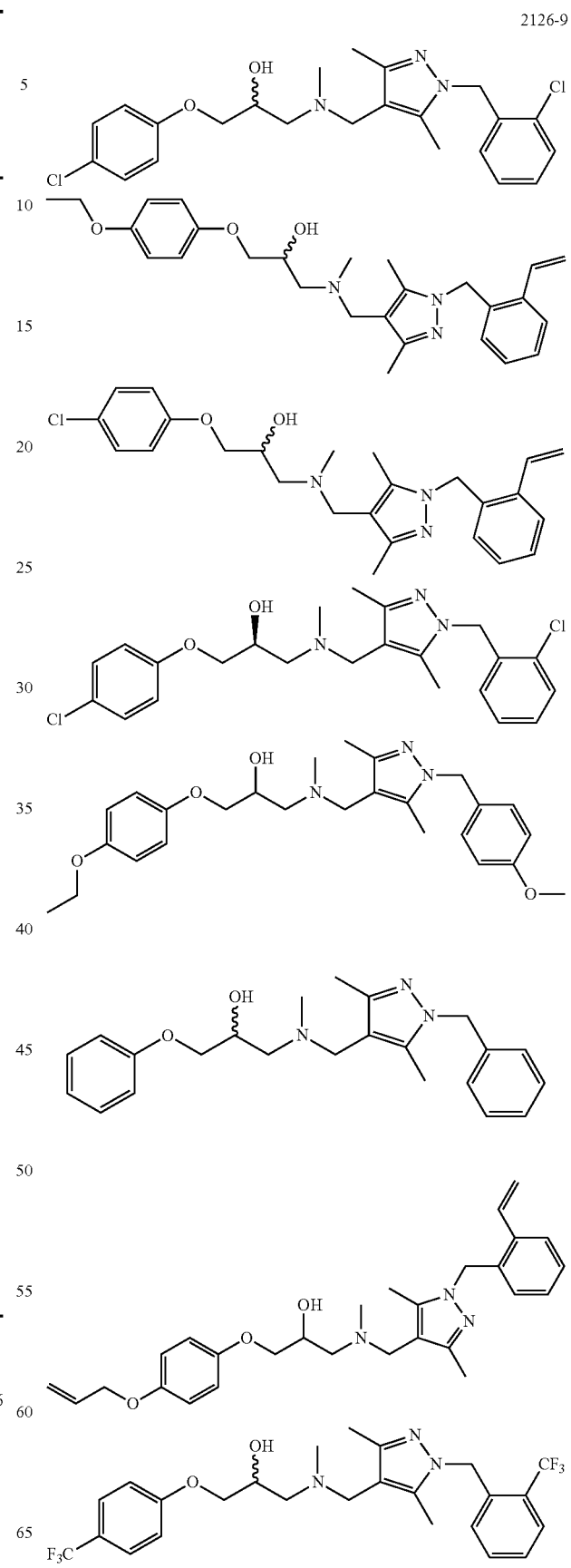

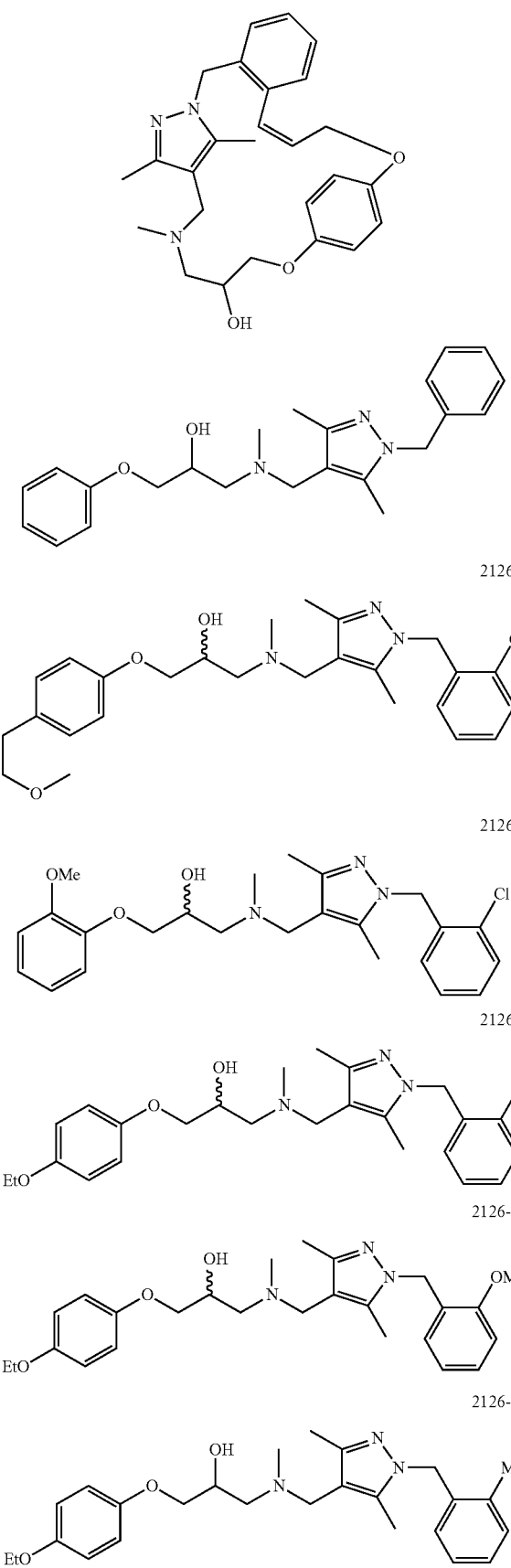

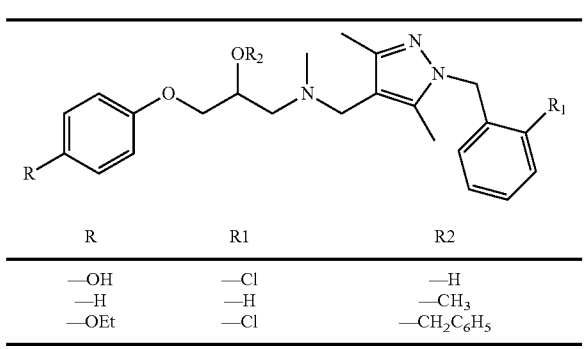

Other exemplary compounds of the invention include the following:

| R | R1 | R2 |
|---|---|---|
| —OH | —Cl | —H |
| —H | —H | —CH₃ |
| —OEt | —Cl | —CH₂C₆H₅ |

Substitution of an OH at the R position extends the structure activity relationship (SAR) with regards to the ethers that were made at that position.

A methyl ether version of compound 2126 showed an excellent activity. Compounds of the invention include other ether derivatives such as benzyl ether. If ether compounds show increased biological activity, then this may indicate that the hydroxyl group is facing a hydrophobic pocket within the binding site. The chiral versions of these compounds and additional ethers are within the scope of the present invention, e.g., $R_2$=Et, iPr, t-Bu, etc.).

Experimental data indicate that both the epoxide and the amine fragments are active. Additional hydrophobic interactions can be introduced to compounds of the invention, e.g., by using the following reaction strategy.

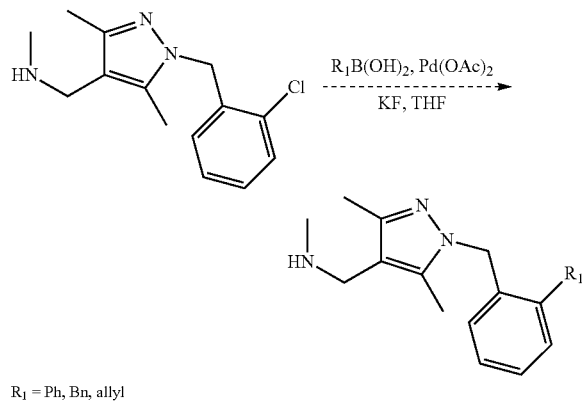

$R_1$ = Ph, Bn, allyl

Computer-Aided Docking Simulation.

The docking studies were performed using AutoDock 4.0. Lamarckian Generic Algorithm (LGA) and the torsion angles of the ligand were varied using AUTOTORS. All other procedures for the docking experiment were followed as described in the user manual for the AutoDock 4.0 program. Docked conformations were ranked automatically by the AutoDock 4.0 program using a force field scoring function. A total of 100 distinct conformational clusters were found out of 100 runs using an rmsd-tolerance of 1.0 Å. Among those, one of the highest three ranked docked structures was used for molecular visualization.

TLR4/MD-2 Pull Down Assay

HeLa cells were grown in Dulbecco's modified eagle medium (DMEM) supplemented with 10% fetal bovine serum (FBS) to a density of $8\times10^6$/ml and transfected by electroporation (250V, 960 µF) with 20 µg of Flag-sTLR4 and 10 µg of MD-2-Flag-His in Dulbecco's PBS/1.25% DMSO. Plasmids were a kind donation from the Fabio laboratory. Cells were re-plated into 10 cm plates in DMEM containing FBS to allow recovery and cell adhesion. After 6-8 h cell media was replaced with serum-free medium 293 SFM2 (Invitrogen, CA, USA). Media was collected after 24 h later. In order to capture His tagged protein complexes, filtered media was incubated with ProBond nickel resin (Invitrogen, CA, USA) overnight. The resin was then washed in phosphate buffered saline (PBS), resuspended in Laemmli sample buffer, boiled and analyzed by SDS-PAGE and immunoblot using anti-Flag mAb. The effect of small molecules on the TLR4/MD-2 interaction was assessed by addition of compounds dissolved in DMSO (and an equal amount of DMSO for the control) to the cells prior to overnight incubation.

Real Time Microscopy of TLR4 Signaling in a Stably Transfected RAW264.7 Mouse Macrophage Cell Line.

TLR4 signaling leads to the simultaneous activation of three parallel intra-cellular signaling pathways. Two of these (through NF-κB and MAPK) are believed to be principally responsible for the proinflammatory responses induced by TLR4 activation, while the third parallel pathway (PI3K/Akt1) is believed to be more related to cell survival, apoptosis and cell motility. As all three are activated by agonism at TLR4, any one of these can be used as a reflection of TLR4 activation. Given the availability of a RAW264.7 mouse macrophage cell line stably transfected to express green fluorescent protein (GFP)-tagged Akt1, mobilization and cytosolic clearance of GFP-Akt1 was used as an indicator of TLR4 activation. Lipopolysaccharide (LPS; *Escherichia Coli*; Serotype: 0111:B4) was obtained from Sigma (St. Louis, Mo., USA). Cells were grown up in growth media supplemented with 10% FBS, 10× penicillin/streptomycin and 10×1-glutamine and then were plated at a density of $2\times10^5$ cells/mL in growth media on 35 mm MatTek Glass Bottom Dishes (Ashland, Mass., USA) for 18 h prior to imaging. Just prior to imaging the growth media was removed from the plates, washed twice with 1 mL Hank's buffered saline solution (HBSS) supplemented with 25 mM HEPES buffered to pH 7.4 and replaced with 1 mL warmed conditioned imaging Hanks Buffer media (media was conditioned by a 24 h incubation with RAW264.7 cells). Imaging was carried out on a Nikon inverted microscope (Melville, N.Y., USA) with a 60× oil immersion objective, GFP/RFP dichroic mirror with corresponding single band excitation and emission filters (Chroma Technology, VT, USA) and CoolSNAP ES camera (Photometrics, Tucson, Ariz., USA). A mercury lamp provided excitation. Images were captured every 7.5 s. Baseline fluorescence was captured for 5 frames, following which vehicle or antagonist was added in 200 µl. Imaging continued for a further 20 frames at which time LPS or test agonist (200 µl) were applied and monitored for a further 20 frames. If no visual response was obtained C5a (200 µl) was added to the plates to confirm if the cells were responsive. GFP-Akt1 cytosolic clearance was quantified using ImageJ and expressed as a normalized change in cytoplasmic fluorescence over time.

RAW264.7 Nitric Oxide Cell TLR Selectivity Assay

RAW cells were grown in DMEM supplemented with 10% FBS, penicillin (100 U/ml), streptomycin (100 mg/ml) and L-glutamine (2 mM). RAW cells were then planted in 96-well plates at 100,000 cells per well and grown for 24 h in the media descried previously. After 24 h media was removed and replaced with Macrophage-SFM (Invitrogen, CA, USA). Lanes were doped with the appropriate TLR specific ligands: LPS (lipopolysaccharide), poly(I:C) (polyinosinic-polycytidylic acid), FSL-1 ((S,R)-(2,3-bispalmitoyloxypropyl)-Cys-Gly-Asp-Pro-Lys-His-Pro-Lys-Ser-Phe), R848 (4-amino-2-(ethoxymethyl)-α,α-dimethyl-1H-imidazo[4,5-c]quinoline-1-ethanol) and Pam$_3$CS K$_4$ (N-palmitoyl-S—[2,3-bis (palmitoyloxy)-(2RS)-propyl]-[R]-cysteinyl-N-seryl-[S]-lysyl-N-lysyl-[S]-lysyl-4-[S]-lysine.3HCl) were used to selectively activate TLR4, TLR3, TLR2/6, TLR7 and TLR2/1 respectively. Two lanes for each ligand were prepared one containing ligand only and the other with the ligand and 300 nM of Compound A-1. Plates were then incubated for 24 h. Following incubation 100 µL of media was removed and added to flat black 96-well microfluor plates (Thermo scientific, MA, USA). 10 µL of 2,3-diaminonaphthalene (0.05 mg/ml in 0.62 M HCl) was added to each well and incubated for 15 min. The reaction was quenched by addition of 5 µL 3 M NaOH and the plate was read on Beckman Coulter DTX880 reader (Beckman Coulter, CA, USA) with excitation at 365 nm and emission at 450 nm. Nitrite (a stable metabolite of nitric oxide) concentration was determined from a nitrite standard curve.

To understand the specificity of inhibitors between different TLRs, the selectivity of compound that showed 99% inhibition in SEAP reporter gene activation assay (see below) was investigated by measuring nitric oxide (NO) production in RAW cells. RAW cells express all TLRs and each specific TLR can be individually activated by treatment with a receptor-specific ligand. Activation of TLRs results in downstream signalling and production of pro-inflammatory mediators such as nitric oxide (NO). This compound (27 µM) inhibited TLR4-mediated NO production but showed negligible effects on the signalling of TLR3, TLR 2/6, TLR 2/1 and TLR7. These results indicated that this compound selectively inhibits LPS-induced TLR4 activation without significantly affecting other homologous toll like receptors.

Secreted Alkaline Phosphatase (SEAP) Assay

Materials for the SEAP assay were obtained from Applied Biosystems (CA, USA) and utilized according to the manufacturer's specifications. Human embryonic kidney 293 (HEK293) cells stably transfected with TLR4 and a secreted alkaline phosphatase (SEAP) reporter gene was obtained from Invivogen (CA, USA). Cells were cultured in DMEM medium supplemented with 10% fetal bovine serum, 10× penicillin/streptomycin, 10×1-glutamine, 1× normocin (ant-nr-1) and 1×HEK Blue (hb-sel). Cells were implanted in 96 well plates 24 h at 37° C. prior to drug treatment. On the day of treatment, media was removed from the 96-well plate, replaced with cerebrospinal fluid (CSF) buffer (124 mM NaCl, 5 mM KCl, 0.1 mM $CaCl_2$, 3.2 mM $MgCl_2$, 26 mM $NaHCO_3$ and 10 mM glucose, pH 7.4) containing 1-20 ng/mL LPS, as well as 0.2-50.0 µM drug or 3-400 ng/mL LPS-RS with 0.5% DMSO.

A sample of CSF buffer (15 µL) from each well was collected and transferred to an opaque white 96 well plate (Microfluor 2, Thermo Scientific MA, USA). Each well was treated with 45 µL of 1× dilution buffer, covered with microseal (MSB1001, Bio-Rad, CA, USA) and incubated for 30 min at 65° C. After 30 min, plates were cooled to room temperature on ice and 50 µL of SEAP assay buffer was added to each well. After a 5 min incubation, 50 µL of disodium 3-(4-methoxyspiro{1,2-dioxetane-3,2-(5-chloro)tricyclo [3.3.1.13,7]decan}-4-yl)phenyl phosphate (CSPD) diluted 1:20 with reaction buffer was added to each well. After 20 min, the luminescence of each well was measured using a plate reader (Beckman Coulter, DTX 880, CA, USA) with multimode analysis software. Some of the results of the SEAP reporter gene activation assay are shown in table below:

| $R^1$ | $R^2$ | % Inhibition |
|---|---|---|
| 2-Cl | 4-OEt | 52% |
| 2-Cl | 4-OEt | 61% |
| 2-Cl | 4-OEt | 0% |
| 4-OMe | 4-OEt | 4% |
| H | H | 1% |
| 2-Cl | 4-($C_2H_4$)OMe | 32% |
| 2-Cl | 2-OMe | 36% |
| 2-Cl | 4-Cl | 99% |
| 2-F | 4-OEt | 40% |
| 2-OMe | 4-OEt | 35% |
| 2-Me | 4-OEt | 31% |

Cell Viability Assay

Human embryonic kidney 293 (HEK293) cells were stably transfected with TLR4 and necessary assembly and signalling proteins (MD2, CD-14, LPSBP, etc.). Cells were cultured in DMEM supplemented with 10% FBS, penicillin (100 U/ml), streptomycin (100 mg/ml), L-glutamine (2 mM), 0.1 mg/ml normocin (InvivoGen, CA, USA) and 1×HEK Blue selection reagent (InvivoGen, CA, USA). Cells were implanted in 6 cm plates and grown to 65-75% confluency by incubating at 37° C., prior to drug treatment. On the day of treatment, media was removed from the 6 cm plate and replaced with cerebrospinal fluid (CSF) buffer supplemented with drug treatment. After 24 h incubation at 37° C., CSF was removed and cells were agitated with 0.05% Trypsin plus 0.2 g/l EDTA (Invitrogen, CA, USA) and re-suspended in fresh DMEM supplemented media. After re-suspension, a 100 sample was taken from each 6 cm plate, mixed gently with 100 µl 0.4% Trypan Blue (Sigma, Mo., USA) and allowed to sit for 5 min. The ratio of blue stained cells to total cells was then quantified using a Bright Line 0.1 mm depth hemocytometer (VWR, PA, USA) under a Nikon TMS light microscope (Nikon Instrumentals, CA USA).

Down regulation of TLR4 and MD-2 by RNAi inhibits Morphine Induced Microglia Activation A murine microglial cell line, BV-2 was grown in DMEM medium supplemented with 10% FBS in Primaria-treated flask (Falcon, BD Bioscience, CA, USA). Cells were detached from flask by trypsin digestion when ~80% confluence was reached. 6 µL of SMARTpool siRNA (Dharmacon, Lafayette, Colo., USA) stock solution (50 µM) was diluted with 14 µl D-PBS, and 8 µl of Lipofectamine LTX (Invitrogen, Carslbad, Calif., USA) was diluted with 12 µl D-PBS. Subsequently TLR4 siRNA and Lipofectamine LTX solutions were gently mixed together in the well of 6 well-plate and incubated at room temperature for 30 min. Then, cells were planted in 6-well plate at a cell density of $5 \times 10^4$ cells per ml. After 48 h RNAi, 200 µM of morphine was added. Plates were then incubated for an additional 24 h. Then cells were collected and lysed by M-PER Mammalian Protein Extraction Reagent (Thermo Scientific, Rockford, Ill., USA). For investigating the effect of down-regulating MD-2 or TLR4 on background inflammatory factors, cells were harvested after 72 h of RNAi. IL-1β and TNF-α levels were analyzed by ELISA (BD Biosceince, San Diego, Calif., USA) according to manufacture's instructions.

Inhibition of Morphine Induced Microglia Activation by Small Molecule Inhibitors BV-2 cells were grown in DMEM medium supplemented with 10% FBS in Primaria-treated flask (Falcon, BD Bioscience, CA, USA). Cells were detached from flask by trypsin digestion when ~80% confluence was reached. Cells were then planted in 6 well-plate at $4 \times 10^5$ cells per well and grown for 24 h. After 24 h, medium was removed and replaced with DMEM supplemented with 1% FBS and morphine (200 µM) was added. In addition, compound 1, 2 or 3 (10 µM) was coadministered with the morphine or alone. Plates were then incubated for an additional 24 h. Then cells were collected and lysed by M-PER Mammalian Protein Extraction Reagent (Thermo Scientific, Rockford, Ill., USA). IL-1β was analyzed by ELISA (BD Biosceince, San Diego, Calif., USA) according to manufacture's instructions.

Behavioral Assessment of Responsivity Radiant Heat (Hargreaves Test)

Pathogen-free adult male Sprague-Dawley rats (n=5-6 rats/group for each experiment; 300-375 gm; Harlan Labs, Madison, Wis., USA) were used in all experiments. Rats were housed in temperature (23±3° C.) and light (12 hr:12 hr light:dark cycle; lights on at 0700) controlled rooms with standard rodent chow and water available ad libitum. All testing was conducted blind with respect to group assignment. Rats received at least three 60 min habituations to the appropriate test environment prior to behavioral testing. Thresholds for behavioral response to heat stimuli applied to the tail were assessed using a modified Hargreaves test. Briefly, baseline withdrawal values were calculated from an average of two consecutive withdrawal latencies of the tail, measured at 15 min intervals. Latencies for the thermal stimulus at baseline ranged from 2 to 3 sec and a cut-off time of 10 sec was imposed to avoid tissue damage. Baseline withdrawal latency assessments were performed prior to, and again across a time course after drug administration. Vehicles were administered equal volume to the drugs under test.

Whole Blood Model of Inflammation

Test of TLR4 inhibition by compounds of the invention with respect to impact on secretion of cytokines IL-6, IL-8, (TNFα) and IL1β in the whole blood model of inflammation was performed using the procedure described by Mollnes et al. (*Blood*, 2002, 100, 1869-1877) using (i) LPS to compare the two variants of 2126-HCl in a restricted set-up, (ii) gram negative bacteria to initiate innate immune response that involves both TLR4/MD2, TLR2, as well as the complement system (compare to anti-CD14 and compstatin).

The hydrochloride salt of compound 2126 (i.e., 2126-HCl) was one the most effective TLR4 inhibitors, in whole blood test. Its effects on cytokine release upon LPS stimulation was observed at concentrations in the micromolar range, and was more effective than the hydrochloride salt of compound 2126-9 at equimolar concentrations (150 μM) in the presence of inflammatory activator LPS. The hydrochloride salt of compound 2126 did not show any significant toxic effects or induced any noticeable hemolysis at these concentrations. The hydrochloride salt of compound 2126 showed one of the highest inhibition of Il-8 secretion upon both LPS and *E. coli* stimulation, compared and in contrast to anti-CD14. Addition of complement inhibitor compstatin further decreased cytokine release in response to *E. coli*. However, the ratio between the tested cytokine levels stayed the same for both anti-CD14 and the hydrochloride salt of compound 2126-directed block of downstream signaling. Compstatin itself appeared specific for Il8 and Il-1β and had little impact on the secretion of the early, CD14-dependent cytokine Il-6. But it increased the inhibitory effect of both anti-CD14 and 2126-HCl on Il-6 levels when *E. coli* was used as activator. Anti-CD14 was very active on reducing Il-6 plasma levels. In contrast, 2126-HCl appeared to inhibit Il-6 as well as TNFα and Il-1β, but significantly less of Il-8.

Interestingly, CD14 inhibition did not alter complement-regulated Il-1β plasma levels upon *E. coli* stimulation despite what appeared to be a 100% reduction when LPS was used as activator. The presumed TLR4 inhibitor 2126-HCl (500 μM) on the other hand did have an impact. It reduced Il-1β plasma levels by about 50%, similar to what was achieved by compstatin (25 μM), and led to a further reduction to 30% in the presence of compstatin.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound of the formula:

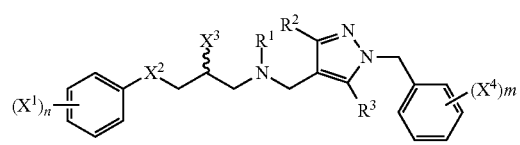

wherein
each of n and m is independently an integer from 0 to 5;
each $X^1$ is independently alkoxide, optionally-substituted alkyl, or alkenyl;
$X^2$ is O, $NR^a$, or S;
$X^3$ is —$OR^b$, —$SR^b$, or —$NR^bR^c$;
each $X^4$ is independently halide or alkoxide; and
each of $R^a$, $R^b$, $R^c$, $R^1$, $R^2$, and $R^3$ is independently hydrogen or alkyl.

2. The compound according to claim 1, wherein $X^2$ is O.

3. The compound according to claim 1, wherein $X^3$ is —OH.

4. The compound according to claim 1, wherein $R^1$, $R^2$ and $R^3$ are alkyl.

5. The compound according to claim 4, wherein $R^1$, $R^2$, and $R^3$ are methyl.

6. The compound according to claim 1, wherein $X^1$ is alkoxide, hetero-substituted alkyl or alkenyl-alkyl.

7. The compound according to claim 1, wherein $X^4$ is alkoxide, Cl, or F.

8. A method for inhibiting toll-like receptor 4 (TLR4) activity to treating pain or a unwanted opioid side-effect in a subject, said method comprising administering to the subject a compound of claim 1.

9. The method of claim 8, wherein said pain comprises chronic pain, nociception, or a combination thereof.

10. A composition comprising an opiate and a compound of claim 1.

11. The composition of claim 10, wherein said opiate and said compound of claim 1 are intimately mixed.

12. The composition of claim 10, wherein the amount of said opiate is from about 50% to about 100% relative to the recommended dosage of said opiate in the absence of said compound of claim 1.

13. The composition of claim 10, wherein the mole ratio of said opiate to said compound of claim 1 ranges from about 1000:1 to about 10:1.

* * * * *